(12) United States Patent
Jones

(10) Patent No.: US 11,918,476 B1
(45) Date of Patent: Mar. 5, 2024

(54) GLENOID REPLACEMENT SYSTEM AND METHODS OF IMPLANTING SAID GLENOID REPLACEMENT

(71) Applicant: ARCA By OrthoAgile, LLC, Raleigh, NC (US)

(72) Inventor: Andrew Jones, Frederick, MD (US)

( * ) Notice: Subject to any disclaimer, the term of this patent is extended or adjusted under 35 U.S.C. 154(b) by 0 days.

(21) Appl. No.: 18/368,512

(22) Filed: Sep. 14, 2023

Related U.S. Application Data

(60) Provisional application No. 63/406,692, filed on Sep. 14, 2022.

(51) Int. Cl.
*A61F 2/40* (2006.01)
*A61F 2/30* (2006.01)
*A61B 17/56* (2006.01)

(52) U.S. Cl.
CPC ........ *A61F 2/4081* (2013.01); *A61F 2/30749* (2013.01); *A61B 2017/564* (2013.01); *A61F 2002/4085* (2013.01)

(58) Field of Classification Search
CPC ......... A61F 2/4081; A61F 2/40; A61F 2/4059
See application file for complete search history.

(56) References Cited

U.S. PATENT DOCUMENTS

| | | | |
|---|---|---|---|
| 4,550,450 A | 11/1985 | Kinnett | |
| 4,919,669 A | 4/1990 | Lannelongue | |
| 9,561,111 B1 | 2/2017 | Goodman | |
| 10,583,012 B1 * | 3/2020 | Longobardi | .......... A61F 2/4014 |
| 2004/0039449 A1 | 2/2004 | Tornier | |
| 2004/0133276 A1 | 7/2004 | Lang | |
| 2006/0079963 A1 | 4/2006 | Hansen | |
| 2007/0179624 A1 | 8/2007 | Stone | |
| 2007/0244563 A1 | 10/2007 | Roche | |
| 2011/0178603 A1 | 7/2011 | Long | |
| 2012/0310359 A1 | 12/2012 | Dro | |
| 2013/0053968 A1 | 2/2013 | Nardini | |
| 2013/0066433 A1 | 3/2013 | Veronesi | |

(Continued)

FOREIGN PATENT DOCUMENTS

| | | |
|---|---|---|
| CN | 113367855 A | 9/2021 |
| FR | 2960418 A1 | 12/2011 |

OTHER PUBLICATIONS

Zimmer Biomet, Comprehensive Vault Reconstruction System brochure (accessed: https://www.zimmerbiomet.com/content/dam/zb-corporate/en/products/specialties/shoulder/comprehensive-valult/comprehensive-vault-reconstruction-system-brochure.pdf), 2016, 8 pp.

*Primary Examiner* — Jason-Dennis N Stewart
(74) *Attorney, Agent, or Firm* — David Meibos; Maywood IP Law

(57) ABSTRACT

A glenoid replacement system, that is securable to a scapula of a patient, may include a glenoid implant. The glenoid implant may further include a prosthetic glenoid articular surface configured to articulate with one of the following: a natural humeral articular surface; an anatomic prosthetic humeral articular surface; and/or a reverse prosthetic humeral articular surface. The glenoid implant may also include a scapular tunnel anchoring feature positioned such that, with the glenoid implant implanted on the scapula, the scapular tunnel anchoring feature is aligned with a scapular tunnel of the scapula to facilitate retention of the glenoid implant on the scapula with a scapular tunnel fastener inserted into the scapular tunnel.

19 Claims, 18 Drawing Sheets

(56) References Cited

U.S. PATENT DOCUMENTS

| | | |
|---|---|---|
| 2014/0257495 A1 | 9/2014 | Goldberg |
| 2014/0257499 A1 | 9/2014 | Winslow |
| 2014/0277520 A1* | 9/2014 | Chavarria ............. A61F 2/4612 623/19.13 |
| 2014/0364953 A1 | 12/2014 | Tomlinson |
| 2018/0271669 A1 | 9/2018 | Goodman |
| 2018/0296356 A1 | 10/2018 | Sbaiz |
| 2020/0214846 A1 | 7/2020 | Perego |
| 2020/0405492 A1 | 12/2020 | Langhorn |
| 2021/0030554 A1 | 2/2021 | Krettek |

\* cited by examiner

GLENOID REPLACEMENT SYSTEM AND METHODS OF IMPLANTING SAID GLENOID REPLACEMENT

CROSS-REFERENCE TO RELATED APPLICATIONS

The present disclosure claims the benefit of U.S. Provisional Patent Application Ser. No. 63/406,692, filed on Sep. 14, 2022 and entitled GLENOID IMPLANT SYSTEM AND METHOD OF IMPLANTING SAID GLENOID IMPLANT, which is incorporated by reference as though set forth herein in its entirety.

TECHNICAL FIELD

The present disclosure relates to devices, systems, and methods for joint prostheses. More specifically, the present disclosure relates to devices, systems, and methods for providing orthopedic implants for the restoration of anatomical mobility of joints, for example, a shoulder joint.

BACKGROUND

Shoulder replacement met with acceptable success in the 1970s by mating a metal replacement for the humeral head to a polyethylene surface covering the diseased scapula side of the joint at the glenoid. While the metal/poly interface had shown good biocompatibility at the hip and knee where the replaced bone represents most of the joint structure, the shoulder continues to be challenging. One of the most common issues is loosening of the prostheses from the glenoid which leads to shoulder replacement failure.

Another challenge is posed by failure of the rotator cuff with age. The confluence of flat tendons into a shirt cuff configuration is designed to contain the humeral head and direct it by muscular action towards the center of the articular surface over the small pedestal of glenoid bone. Poor functioning or absence of rotator cuff tendons condemned conventional ('anatomic') shoulder replacement in all its forms. However, more recent innovative reverse shoulder replacement designs now provide a reliable solution in cuff deficiency but fail to restore normal shoulder mechanics, yielding a lack of overhead motion and a higher rate of dislocation. Furthermore, the glenoid fixation by the device's glenosphere is a weak link especially in high demand patients.

SUMMARY

The various systems and methods of the present disclosure have been developed in response to the present state of the art, and in particular, in response to the problems and needs in the art that have not yet been fully solved by currently available glenoid replacement systems and methods.

In some embodiments, a glenoid replacement system that is securable to a scapula of a patient may include a glenoid implant. The glenoid implant may further include a prosthetic glenoid articular surface configured to articulate with one of the following: a natural humeral articular surface; an anatomic prosthetic humeral articular surface; and/or a reverse prosthetic humeral articular surface. The glenoid implant may also include a scapular tunnel anchoring feature positioned such that, with the glenoid implant implanted on the scapula, the scapular tunnel anchoring feature is aligned with a scapular tunnel of the scapula to facilitate retention of the glenoid implant on the scapula with a scapular tunnel fastener inserted into the scapular tunnel.

In the glenoid replacement system of any preceding paragraph, the scapular tunnel fastener may include a screw and the scapular tunnel anchoring feature may include a hole that receives a shank of the screw.

In the glenoid replacement system of any preceding paragraph, the glenoid replacement system may include a first superior anchoring feature including one of a coracoid process anchoring feature or an acromion process anchoring feature.

In the glenoid replacement system of any preceding paragraph, the first superior anchoring feature may include a clamp.

In the glenoid replacement system of any preceding paragraph, the glenoid replacement system may further include a second superior anchoring feature including the other of a coracoid process anchoring feature and an acromion process anchoring feature.

In the glenoid replacement system of any preceding paragraph, the anatomic prosthetic humeral articular surface may include an anatomic prosthetic glenoid articular surface with a concave shape.

In the glenoid replacement system of any preceding paragraph, the prosthetic glenoid articular surface may include a reverse prosthetic glenoid articular surface with a convex shape.

In the glenoid replacement system of any preceding paragraph, the reverse prosthetic glenoid articular surface may be formed, at least partially, of a polymer.

In some embodiments, a glenoid replacement system that is securable to a scapula of a patient may include a glenoid implant. The glenoid implant may further include a prosthetic glenoid articular surface configured to articulate with one of the following: a natural humeral articular surface; an anatomic prosthetic humeral articular surface; and/or a reverse prosthetic humeral articular surface. The glenoid implant may further include a first superior anchoring feature that may be a coracoid process anchoring feature configured to secure the glenoid implant to a coracoid process of the scapula; and/or an acromion process anchoring feature configured to secure the glenoid implant to an acromion process of the scapula.

In the glenoid replacement system of any preceding paragraph, the first superior anchoring feature may include a coracoid process anchoring feature comprising a coracoid clamp configured to grip a coracoid process.

In the glenoid replacement system of any preceding paragraph, the coracoid anchoring feature may further have one or more apertures configured to receive one or more fasteners configured to secure the coracoid anchoring feature to the coracoid process.

In the glenoid replacement system of any preceding paragraph, the first superior anchoring feature may include an acromion process anchoring feature comprising an acromion clamp configured to grip an acromion process.

In the glenoid replacement system of any preceding paragraph, the acromion anchoring feature may further have one or more apertures configured to receive one or more fasteners configured to secure the acromion anchoring feature to the acromion process.

In the glenoid replacement system of any preceding paragraph, the glenoid implant may also include a second superior anchoring feature comprising a coracoid clamp configured to grip a coracoid process.

In some embodiments, a glenoid replacement system that is securable to a scapula of a patient may include a glenoid implant. The glenoid implant may further include a prosthetic glenoid articular surface configured to articulate with one of the following: a natural humeral articular surface; an anatomic prosthetic humeral articular surface; and/or a reverse prosthetic humeral articular surface. The glenoid implant may further include a superior bracing surface configured such that, with the glenoid implant implanted on the scapula, the superior bracing surface is oriented superiorly and positioned to abut an acromion of the scapula to limit superior migration of the glenoid implant on the scapula.

In the glenoid replacement system of any preceding paragraph, the superior bracing surface may be part of an acromion anchoring feature configured to anchor the glenoid implant to an acromion.

In the glenoid replacement system of any preceding paragraph, the acromion anchoring feature may include a clamp configured to grip an acromion process of the acromion.

In some embodiments, a glenoid replacement system that is securable to a scapula of a patient may include a glenoid implant. The glenoid implant may further include a prosthetic glenoid articular surface configured to articulate with one of the following: a natural humeral articular surface; an anatomic prosthetic humeral articular surface; and/or a reverse prosthetic humeral articular surface. The glenoid implant may further include a first clamp configured to grip a bony protuberance of the scapula to secure the glenoid implant relative to the bony protuberance.

In the glenoid replacement system of any preceding paragraph, the first clamp may be positioned to grip an acromion process of an acromion of a scapula.

In the glenoid replacement system of any preceding paragraph, the first clamp may be positioned to grip a coracoid process of a scapula.

In the glenoid replacement system of any preceding paragraph, the glenoid implant may also include a second clamp configured to grip an acromion process of an acromion of a scapula.

In some embodiments, a method for securing a glenoid replacement implant to a scapula may include: positioning the glenoid implant proximate the scapula, the glenoid implant comprising a prosthetic glenoid articular surface and a scapular tunnel anchoring feature; positioning the glenoid implant on the scapula such that the prosthetic glenoid articular surface is positioned to articulate with one of: a natural humeral articular surface, an anatomic prosthetic humeral articular surface, or a reverse prosthetic humeral articular surface; and anchoring the glenoid implant to the scapula by inserting a scapular tunnel fastener into the scapular tunnel of the scapula to secure the scapular tunnel anchoring feature relative to the scapular tunnel.

In the method of any preceding paragraph, the scapular tunnel fastener may include a screw and the scapular tunnel anchoring feature may have a hole that receives a shank of the screw.

In the method of any preceding paragraph, the method may further include securing a first superior anchoring feature having one of a coracoid process anchoring feature and an acromion process anchoring feature.

In the method of any preceding paragraph, the first superior anchoring feature may include a clamp, and the method further include: engaging the scapula with the clamp prior to positioning the glenoid implant on the scapula.

In the method of any preceding paragraph, the method may further include securing a second superior anchoring feature having the other of the coracoid process anchoring feature and the acromion process anchoring feature.

In some embodiments, a method for securing a glenoid replacement implant to a scapula may include: positioning the glenoid implant proximate the scapula, the glenoid implant comprising a prosthetic glenoid articular surface and a scapular tunnel anchoring feature; positioning the glenoid implant on the scapula such that the prosthetic glenoid articular surface is positioned to articulate with one of: a natural humeral articular surface, an anatomic prosthetic humeral articular surface, or a reverse prosthetic humeral articular surface; and anchoring the glenoid implant by engaging a first superior anchoring feature selected from the group consisting of: a coracoid process anchoring feature configured to secure the glenoid implant to a coracoid process of the scapula; and an acromion process anchoring feature configured to secure the glenoid implant to an acromion process of an acromion of the scapula.

In the method of any preceding paragraph, the first superior anchoring feature may include the coracoid process anchoring feature having a coracoid clamp configured to grip the coracoid process.

In the method of any preceding paragraph, the coracoid process anchoring feature may further include one or more apertures configured to receive one or more fasteners configured to secure the coracoid process anchoring feature to the coracoid process. The method may further include: anchoring the glenoid implant to the scapula by inserting the one or more fasteners into the coracoid process of the scapula to secure the coracoid process anchoring feature relative to the coracoid process.

In the method of any preceding paragraph, the first superior anchoring feature may include the acromion process anchoring feature having an acromion clamp configured to grip the acromion process.

In the method of any preceding paragraph, the acromion process anchoring feature may include one or more apertures configured to receive one or more fasteners configured to secure the acromion process anchoring feature to the acromion process. The method may further include: anchoring the glenoid implant to the scapula by inserting the one or more fasteners into the acromion process of the scapula to secure the acromion process anchoring feature relative to the acromion process.

In the method of any preceding paragraph, the method may further include securing a second superior anchoring feature having a coracoid clamp configured to grip the coracoid process.

In the method of any preceding paragraph, the acromion clamp may permit movement of the acromion process anchoring feature relative to the acromion process and may allow the glenoid implant to be rotated into position proximate the scapula.

In some embodiments, a method for securing a glenoid replacement implant to a scapula may include: positioning the glenoid implant proximate the scapula, the glenoid implant comprising a prosthetic glenoid articular surface and a scapular tunnel anchoring feature; positioning the glenoid implant on the scapula such that the prosthetic glenoid articular surface is positioned to articulate with one of: a natural humeral articular surface, an anatomic prosthetic humeral articular surface, or a reverse prosthetic humeral articular surface; and anchoring the glenoid implant by engaging a superior bracing surface configured such that, with the glenoid implant implanted on the scapula, the superior bracing surface is oriented superiorly and positioned to abut an acromion of the scapula to limit superior migration of the glenoid implant on the scapula.

In the method of any preceding paragraph, the superior bracing surface may be part of an acromion process anchoring feature configured to anchor the glenoid implant to the acromion.

In the method of any preceding paragraph, the acromion process anchoring feature may include a clamp configured to grip an acromion process of the acromion.

In some embodiments, a method for securing a glenoid replacement implant to a scapula may include: positioning the glenoid implant proximate the scapula, the glenoid implant comprising a prosthetic glenoid articular surface and a scapular tunnel anchoring feature; positioning the glenoid implant on the scapula such that the prosthetic glenoid articular surface is positioned to articulate with one of: a natural humeral articular surface, an anatomic prosthetic humeral articular surface, or a reverse prosthetic humeral articular surface; and anchoring a first clamp configured to grip a bony protuberance of the scapula to secure the glenoid implant relative to the bony protuberance.

In the method of any preceding paragraph, the first clamp may be positioned to grip an acromion process of an acromion of the scapula.

In the method of any preceding paragraph, the first clamp may be positioned to grip a coracoid process of the scapula.

In the method of any preceding paragraph, the method may further include engaging a second clamp configured to grip an acromion process of an acromion of the scapula.

These and other features and advantages of the present disclosure will become more fully apparent from the following description and appended claims or may be learned by the practice of the implants, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which.

Figure 1:
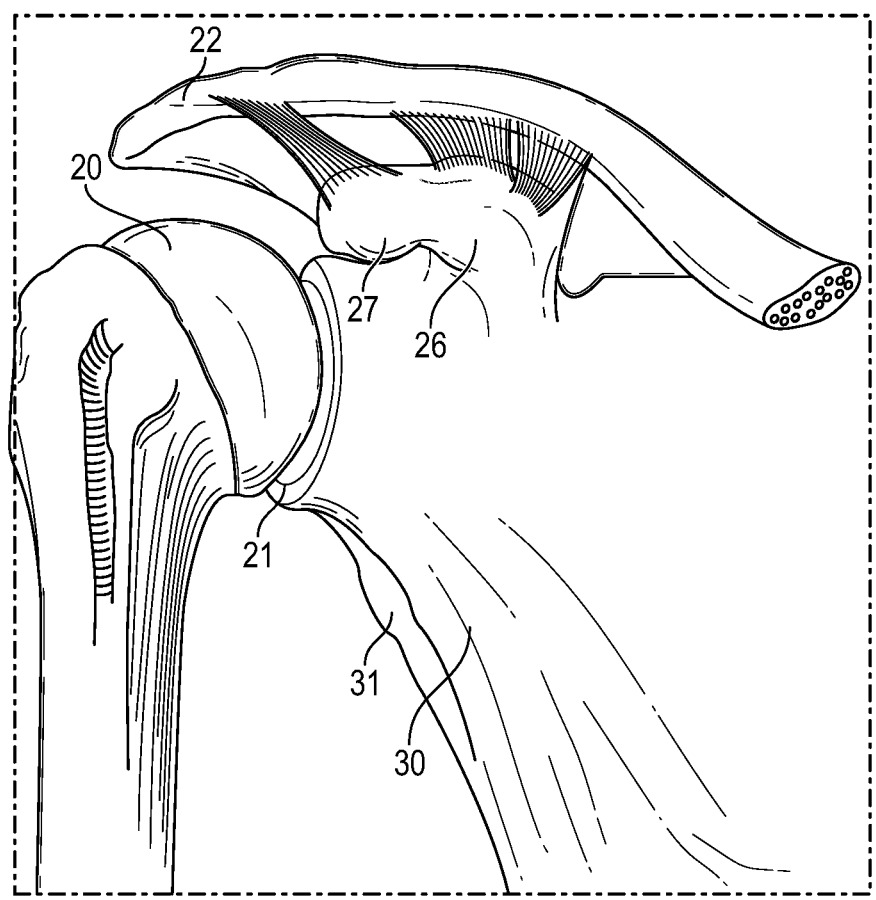
FIG. 1 is a perspective view of some of the bones generally forming the shoulder including the scapula, humerus, acromion and coracoid process.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the devices, systems, and methods, as represented in the drawings, is not intended to limit the scope of the present disclosure but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. Varus means deviation of the distal part of the leg below the knee inward, resulting in a bowlegged appearance. Valgus means deviation of the distal part of the leg below the knee outward, resulting in a knock-kneed appearance.

The present disclosure relates to glenoid implant devices, systems, and methods. Those skilled in the art will recognize that the following description is merely illustrative of the principles of the technology, which may be applied in various ways to provide many alternative embodiments. The present disclosure illustrates glenoid implant devices for the purposes of illustrating the concepts of the present design. However, it will be understood that other variations and uses are contemplated including, but not limited to, applications in the arm, wrist, finger, toe, spine, pelvis, any other bone or joint, etc.

As shown in FIG. 1, a shoulder joint may be formed by a plurality of bones including a scapula 30, a glenoid bone 21, a humerus 20, an acromion process 22 and a coracoid process 26 comprising a coracoid flange bone 27. The scapula 30 may have an enlarged portion along the posterior edge referred to as a scapular tunnel 31.

FIG. 2 through FIG. 8 illustrate a glenoid replacement system 10 comprising a glenoid implant 14 according to an embodiment. In an embodiment, a glenoid replacement system 10 may comprise a glenoid implant 14 configured to extend over the glenoid bone 21 and be retained in position by an acromion base retainer 60 and a coracoid flange retainer 80. The glenoid replacement system 10 may comprise accessory extensions or arms to the adjacent bone prominences configured to improve glenoid fixation. Patient-specific capability in implant design may allow formation of implants that have geometries specific to each patient. The anatomy of a patient may be determined through computed tomography (CT) scan and a unique implant with dimensions and geometries to correspond with the patient's anatomy may be produced. A patient specific implant technology may enable or improve an interference fit of a glenoid cover portion 40, acromion base retainer 60 and/or a coracoid flange retainer 80. An interference fit may enhance glenoid stability and foster biologic fixation of the glenoid implant 14 and a bone portion. Better fixation of the glenoid implant 14 may in turn expand the use of joint constraint on the glenoid side, allowing head containment and a more normal center of rotation that may avoid use of the reverse design for most patients.

In an embodiment, a glenoid cover portion 40 may have a patient implant geometry that may be determined by scanning a patient to determine a patient shoulder geometry based on the patient shoulder anatomy and specifically on a patient glenoid geometry. The patient implant geometry of the anterior surface 24 of the glenoid cover portion 40 may be configured to match the patient glenoid geometry from the scan. A prosthetic glenoid articular surface 44 may comprise a curvature to generally match the patient humerus geometry to provide smooth motion of the humerus within the prosthetic glenoid articular surface 44. In an embodiment, the prosthetic glenoid articular surface 44 may manufactured using a highly crosslinked UHMWPE, a vitamin-E infused highly crosslinked Polyethylene, other biocompatible polymer, titanium alloy, titanium, stainless steel, cobalt chrome or a combination of the listed materials.

In an embodiment, a glenoid replacement system 10 may be comprise a porous surface. The porous surface may be configured to promote bone in growth to complement other features configured to secure the glenoid replacement system 10 to a scapula 30. The porous surface may be configured as a trabecular structure configured to promote bone in-growth. Additionally, or alternatively, the porous surface may be configured to comprise less metal mass implanted and more open areas for bone to grow through a glenoid replacement system 10 and create a more rigid fusion of the glenoid replacement system 10 to the scapula 30. In an embodiment, the porous surface may be applied to a glenoid cover medial surface 42 configured to engage a bone portion. In an embodiment, the glenoid replacement system 10 may be additively manufactured with integrated porous features configured for bone integration. Alternatively, the porous surface may be additively manufactured with integrated porous features configured for bone integration and the porous surface may be subsequently secured to a glenoid replacement system 10.

In an embodiment, a glenoid implant 14 may expand the field of shoulder replacement revision surgery in cases of significant glenoid bone loss. Because the glenoid replacement system 10 may be patient-specific, it may substitute for the patient's areas of bone loss. The fixation of a glenoid implant 14 to an acromion base bone 23 and the coracoid flange bone 27 may provide unique accessory points of glenoid fixation for patients with significant glenoid bone loss. In addition to the acromion arm 61 and coracoid arm 81, a scapular tunnel fastener 32 may be secured through the glenoid cover portion 40 into the scapula 30; scapular tunnel 31, or scapular blade for cases with significant glenoid bone loss. In an embodiment, a glenoid implant 14 may comprise three points of stability: an interference fit of the glenoid cover portion 40, which may have a scapular tunnel fastener 32 to secure the glenoid cover portion 40 to the scapula 30; an acromion base retainer 60, which may be configured for an interference fit with an acromion base bone 23 and/or comprise one or more apertures configured to receive one or more acromion fasteners 69, 69' configured to secure the acromion base retainer 60 to the acromion base bone 23; and a coracoid flange retainer 80, which may be configured for an interference fit with a coracoid flange bone 27 and/or comprise one or more apertures configured to receive one or more coracoid fasteners 89, 89' configured to secure the coracoid flange retainer 80 to the coracoid flange bone 27.

In an embodiment, a glenoid cover portion 40 of the glenoid implant 14 may be configured to be implanted over a glenoid bone 21 or glenoid bone area in cases where the glenoid bone has deteriorated. The glenoid implant 14 may comprise a prosthetic glenoid articular surface 44 comprising a concave shape 47 and configured to receive one of: a natural humeral articular surface; an anatomic prosthetic humeral articular surface; and a reverse prosthetic humeral articular surface. In an embodiment, the prosthetic glenoid articular surface 44 may comprise a concave shape 47. In another embodiment, an anatomic prosthetic humeral articular surface comprises a reverse prosthetic articular surface with a convex shape. In an embodiment, a glenoid implant 14 may comprise a glenoid cover portion 40 comprising a glenoid cover medial surface 42 configured to engage a glenoid bone 21. The glenoid cover portion 40 may also comprise a scapula interface 46 configured to extend over, and in some cases, attach to a scapula 30. The scapula blade may extend along its lateral border to more than three times its midportion's thickness to form a long tube of cortical bone referred to as a scapular tunnel 31. The scapular tunnel 31 may extend inferiorly from the edge of the scapula's glenoid articular surface. The scapular tunnel 31 may be assessed and integrated into a fixation strategy. In some embodiments, the scapula interface 46 may be configured to engage the scapular tunnel 31 and may be secured with a scapular tunnel fastener 32. The scapular tunnel fastener 32 may be configured to extend through a glenoid cover portion 40 and into the scapular tunnel 31. Improved medial fixation of a glenoid implant 14 to a glenoid bone 21 may be advantageous, especially for cases with significant bone loss of the glenoid bone 21 that is common and as yet unsolved in cases of failure of prior glenoid replacement.

In an embodiment, a glenoid cover portion 40 may comprise a superior portion 41 proximal to the top of the glenoid cover portion 40 when implanted and when a person is standing upright, or on the opposing side of the glenoid cover portion 40 from the scapula interface 46 and scapular tunnel 31. In an embodiment, a glenoid implant 14 may comprise a first superior anchoring feature configured to secure the glenoid implant 14 to a portion of a scapula 30. In an embodiment, the first superior anchoring feature may be configured as a coracoid process anchoring feature 84 configured to secure the glenoid implant 14 to a coracoid process 26 of the scapula 30. In an embodiment, the first superior anchoring feature may be configured as an acromion process anchoring feature 64 configured to secure the glenoid implant 14 to an acromion process 22 of the scapula 30.

In an embodiment, a glenoid implant 14 may comprise a second superior anchoring feature configured to secure the glenoid implant 14 to a portion of a scapula 30. In an embodiment, the second superior anchoring feature may be configured as a coracoid process anchoring feature 84 configured to secure the glenoid implant 14 to a coracoid process 26 of the scapula 30. In an embodiment, the second superior anchoring feature may be configured as an acromion process anchoring feature 64 configured to secure the glenoid implant 14 to an acromion process 22 of the scapula 30.

In an embodiment, a glenoid implant may comprise a first superior anchoring feature configured to secure the glenoid implant 14 to a portion of a scapula 30 and a second superior anchoring feature configured to secure the glenoid implant 14 to a portion of a scapula 30, wherein the first superior anchoring feature is configured as a coracoid process anchoring feature 84 configured to secure the glenoid implant 14 to a coracoid process 26 of the scapula 30 and the second superior anchoring feature may be configured as an acromion process anchoring feature 64 configured to secure the glenoid implant 14 to an acromion process 22 of the scapula 30.

In an embodiment, a glenoid implant 14 may comprise an acromion base retainer 60 configured to couple with an acromion base bone 23 to retain the glenoid cover portion 40 in position over the glenoid bone 21. The acromion base retainer 60 may comprise an acromion process anchoring feature 64. The acromion process anchoring feature 64 may comprise a U-shape and may be configured to engage the acromion base bone 23. The acromion process anchoring feature 64 may further be configured to be coupled to the glenoid cover portion 40 by an acromion arm 61. The acromion arm 61 may comprise an acromion arm width 62 and an acromion arm height 63 configured to effectively support connection of the glenoid cover portion 40 to the acromion base bone 23. The acromion arm 61 may further allow positioning of the acromion process anchoring feature 64 around the acromion base bone 23. In an embodiment, the acromion arm width 62 may be greater than the acromion arm height 63, such as twice or more, three times or more, four times or more and any range between and including the ratios provided. The ratio of the acromion arm width 62 to the acromion arm height 63 may more effectively allow manipulation of the acromion process anchoring feature 64 around the acromion base bone 23 while also providing rigidity of the acromion process anchoring feature 64. In an embodiment, the ratio of the acromion arm width 62 to the acromion arm height 63 may effectively allow bending in the height direction while reducing bending in the width direction due to the moment of inertia of this geometry. In an embodiment, the ratio of the acromion arm width 62 to the acromion arm height 63 may reduce valuable area required for the acromion arm 61 and may reduce interference with muscle, ligaments, tendons, bone and the like. The acromion process anchoring feature 64 may have an opening width that requires the acromion process anchoring feature 64 to expand to slide over the acromion base bone 23. This patient specific geometry may provide for a more secure and stable implant.

In an embodiment, an acromion process anchoring feature 64 may comprise an acromion anterior flange 66 extending over an anterior surface 24 of the acromion base bone 23 and an acromion posterior flange 68 extending over a posterior surface 25 of the acromion base bone 23. The acromion base bone 23 may be received into an acromion clamp 65 formed by the acromion anterior flange 66, acromion posterior flange 68, and an acromion bracket base 67. The acromion clamp 65 may extend between and connect the acromion anterior flange 66 and the acromion posterior flange 68. In an embodiment, the height of the acromion process anchoring feature 64 may be greater than the height of the acromion arm 61 by a factor of 1.5 or more, 2.0 or more, 3.0 or more, 5.0 or more and any range between and including the ratios provided. In an embodiment, the acromion arm 61 may be coupled to the acromion bracket base 67. In an embodiment, the acromion anterior flange 66 and the acromion posterior flange 68 may extend away from the acromion bracket base 67 and the acromion arm 61 in generally the direction of the acromion arm length 71. In an embodiment, the acromion anterior flange 66 and the acromion posterior flange 68 may form an acromion clamp 65 for receiving the acromion base bone 23 therein.

In an embodiment, an acromion arm 61 may be attached to an acromion bracket base 67 configured to extend between, and couple together, an acromion anterior flange 66 and an acromion posterior flange 68. The acromion arm 61 may comprise an acromion arm length 71 from a connection with a glenoid cover portion 40 to a connection with an acromion process anchoring feature 64 that may be at least twice the acromion arm width 62 or acromion arm height 63. In an embodiment, the acromion arm length 71 may be about 10 mm or more, about 20 mm or more, about 30 mm or more, about 40 mm or more, about 50 mm or more and any range between and including the values provided. The acromion arm length 71 may depend on the anatomy of the patient receiving the glenoid implant 14.

As shown throughout the figures, an optional acromion arch retainer 50 may comprise an acromion arch arm 51 that may extend between a glenoid cover portion 40, such as from a superior portion 41 and an acromion arch 222. The acromion arch arm 51 may extend from the glenoid cover portion 40 between the acromion arm 61 and coracoid arm 81, with respect to the perimeter of the glenoid cover portion 40. The acromion arch retainer 50 may have an acromion arch flange 54 configured on the extended end of the acromion arch arm 51. In an embodiment, the acromion arch flange 54 may be configured to receive an acromion process anchoring feature configured to secure the acromion arch flange 54 to the acromion arch 222. In an embodiment, the acromion arch flange 54 may be configured as a superior bracing surface configured such that, with the glenoid implant 14 implanted on the scapula 30, the superior bracing surface may be oriented superiorly and positioned to abut an acromion arch 222 of the scapula 30 to limit superior migration of the glenoid implant on the scapula 30.

In an embodiment, a coracoid flange retainer 80 may comprise a coracoid process anchoring feature 84. The coracoid process anchoring feature 84 may comprise a U-shape and may be configured to engage the coracoid flange bone 27. The coracoid process anchoring feature 84 may further be configured to be coupled to the glenoid cover portion 40 by a coracoid arm 81. The coracoid arm 81 may comprise a coracoid arm width 82 and a coracoid arm height 83 to effectively support connection of the glenoid cover portion 40 to the coracoid flange bone 27. In an embodiment, the coracoid arm height 83 may be greater than the coracoid arm width 82, such as twice or more, three times or more, four time or more and any range between and including the ratios provided. The ratio of the coracoid arm height 83 to the coracoid arm width 82 may more effectively allow manipulation of the coracoid process anchoring feature 84 around the coracoid flange bone 27 while also providing rigidity of the coracoid process anchoring feature 84. In an embodiment, the ratio of the coracoid arm height 83 to the coracoid arm width 82 may effectively allow bending in the coracoid arm width 82 direction while reducing bending in the coracoids arm height 83 direction due to the moment of inertia of this geometry. In an embodiment, the ratio of the coracoid arm height 83 to the coracoid arm width 82 may reduce valuable area required for the coracoid arm 81 and may reduce interference with muscle, ligaments, tendons, bone and the like. In an embodiment, the direction of stiffness of the coracoid arm 81 may be in a direction generally perpendicular to the direction of stiffness of the acromion arm 61. In an embodiment, the glenoid implant may be configured so that the generally perpendicular direction of stiffness of the coracoid arm 81 relative to the direction of stiffness of the acromion arm 61 may more effectively retain the glenoid cover portion 40 in position after implantation in a patient.

In an embodiment, a coracoid process anchoring feature 84 may comprise a coracoid anterior flange 86 configured to extend over an anterior surface 28 of a coracoid flange bone 27 and a coracoid posterior flange 88 configured to extend over a posterior surface 29 of the coracoid flange bone 27. In an embodiment, a coracoid process anchoring feature 84 may comprise a coracoid clamp 85. The coracoid clamp 85 may be formed by the coracoid anterior flange 86, the coracoid posterior flange 88, and the coracoid bracket base 87 and may extend between and connect the coracoid anterior flange 86 and the coracoid posterior flange 88. The coracoid clamp 85 may be configured to receive a coracoid flange bone 27. In an embodiment, a coracoid bracket width 94 may be greater than a coracoid arm width 82 by a factor of 1.5 or more, 2.0 or more, 3.0 or more, 5.0 or more and any range between and including the ratios provided. In an embodiment, the coracoid arm 81 may be coupled the coracoid posterior flange 88 or to the coracoid bracket base 87. In an embodiment, the coracoid anterior flange 86 and the coracoid posterior flange 88 may extend generally in the direction of the coracoid arm height 83. In an embodiment, the coracoid anterior flange 86 and the coracoid posterior flange 88 may form a coracoid clamp 85 for receiving the coracoid flange bone 27 therein.

In an embodiment, a coracoid arm 81 may be attached to a coracoid posterior flange 88. A coracoid bracket base 87 may extend between and couple together a coracoid anterior flange 86 and the coracoid posterior flange 88. The coracoid arm 81 may comprise a coracoid arm length 91 from a connection with a glenoid cover portion 40 to a connection with a coracoid process anchoring feature 84 that may be at least twice the coracoid arm width 82 or coracoid arm height 83. In an embodiment, the coracoid arm length 91 arm may be about 10 mm or more, about 20 mm or more, about 30 mm or more, about 40 mm or more, about 50 mm or more and any range between and including the values provided. The coracoid arm length 91 may depend on the anatomy of the patient receiving the glenoid implant 14.

In an embodiment, the coracoid flange retainer 80 may have a patient implant geometry that may be determined by scanning a patient to determine a patient shoulder geometry based on the patient shoulder anatomy and specifically on a patient coracoid flange bone and a geometric distance between the coracoid flange bone 27 and a glenoid. The coracoid arm length 91 may be configured to grip the coracoid process anchoring feature 84 around the coracoid flange bone 27 with the glenoid cover portion 40 engaged over the glenoid. The coracoid bracket width 94 may have a patient matched geometry that may produce an interference fit between the coracoid process anchoring feature 84 and the coracoid flange bone 27. The coracoid bracket width 94 may be configured to allow the coracoid process anchoring feature 84 to expand to slide over a coracoid flange bone 27. The patient specific geometry may provide for a more secure and stable glenoid implant 14 engagement with a patient's anatomy.

Figure 2:
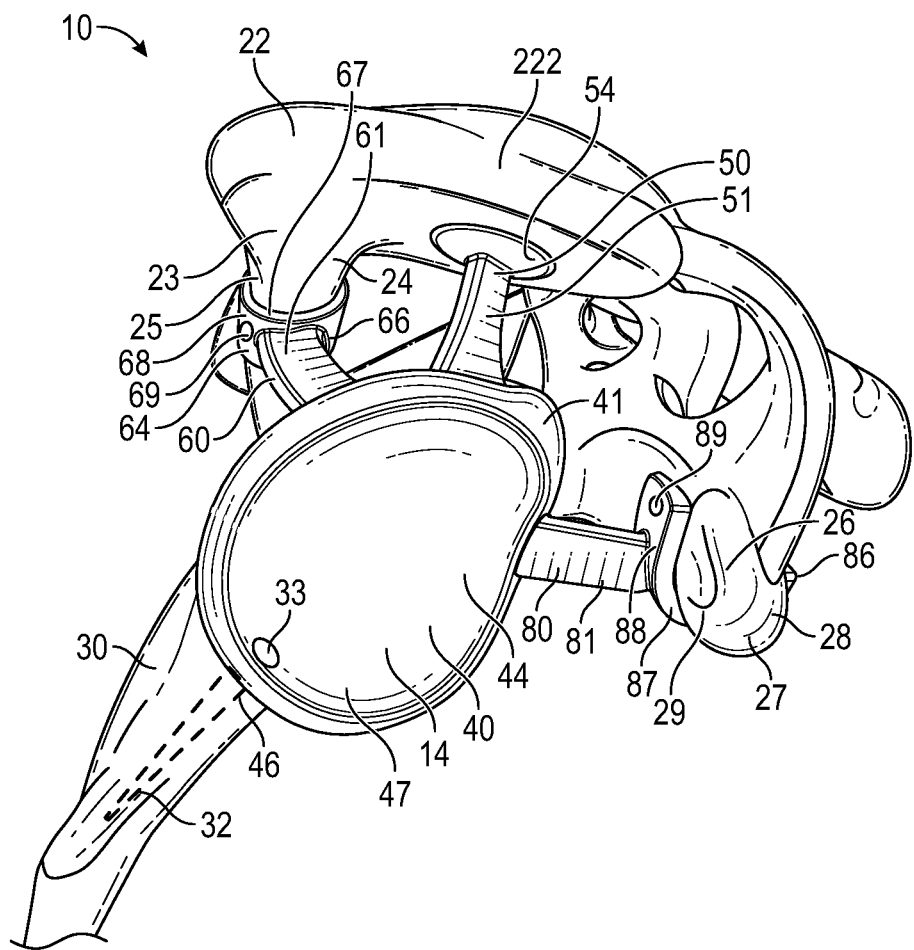
FIG. 2 is a perspective view of a glenoid replacement system implanted over a glenoid bone and coupled with the acromion base bone and the coracoid flange bone according to an embodiment.
Figure 3:
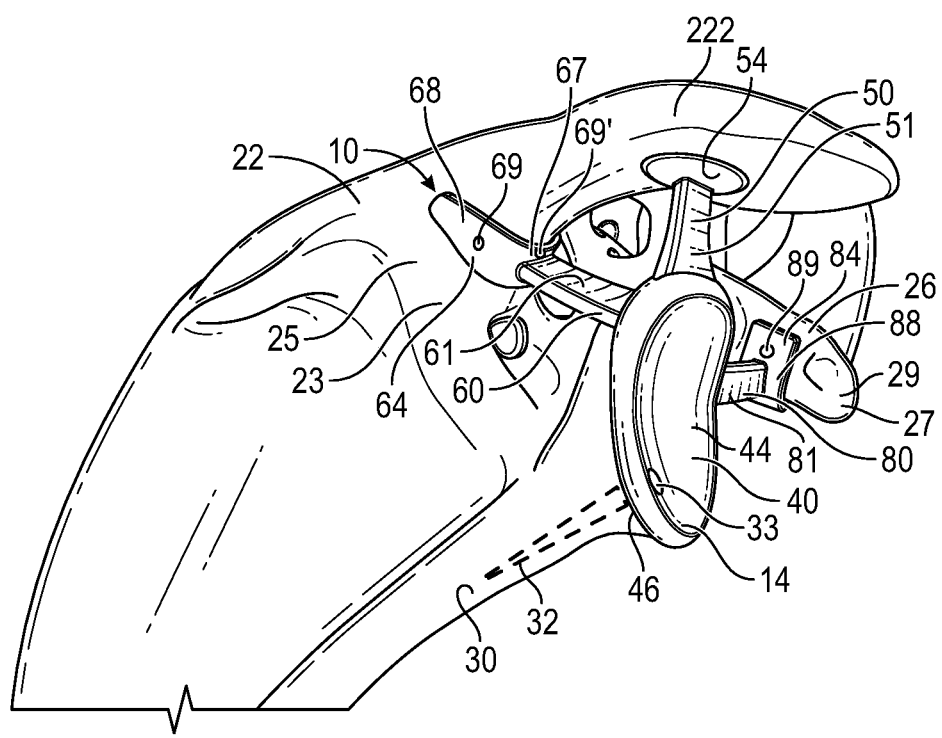
FIG. 3 is a perspective view of the glenoid replacement system of FIG. 2 implanted over a glenoid bone and coupled with the acromion base bone and the coracoid flange bone.
Figure 4:
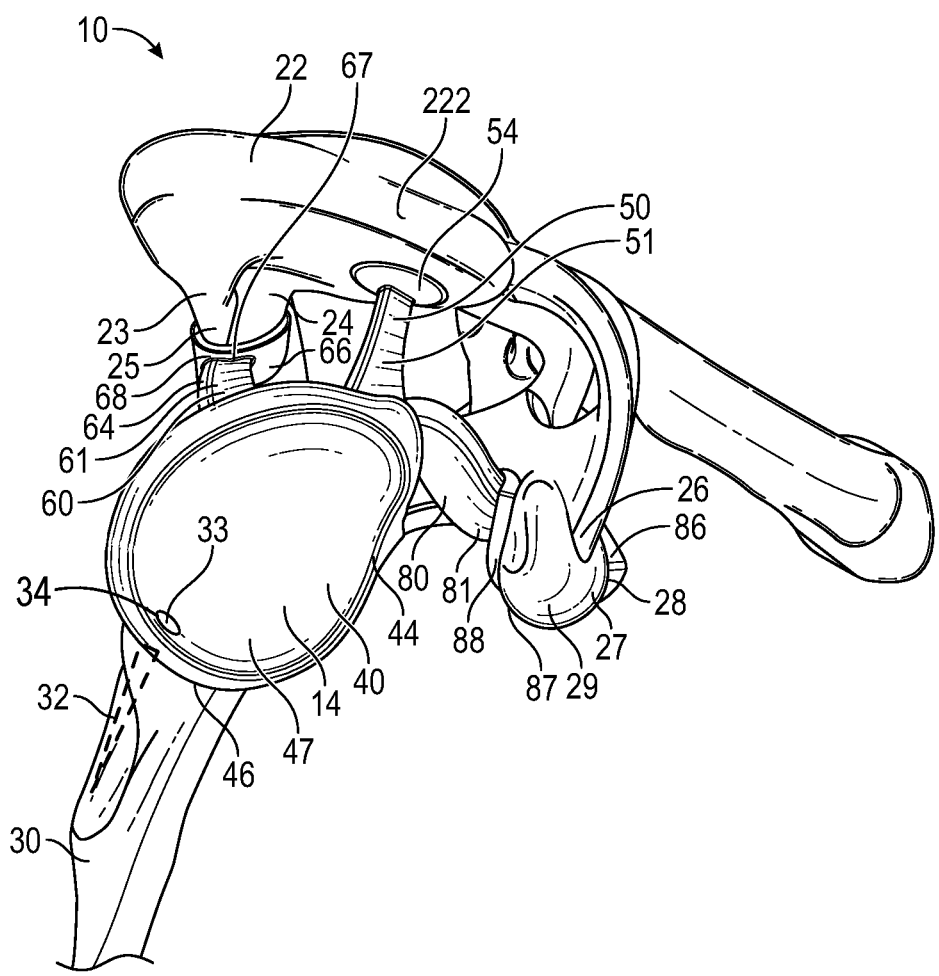
FIG. 4 is a perspective view of the glenoid replacement system of FIG. 2 implanted over a glenoid bone and coupled with the acromion base bone and the coracoid flange bone.

In an embodiment, as shown in FIG. 2 through FIG. 4, a glenoid cover anterior surface 43 may be configured to match the geometry of a patient's glenoid bone. An acromion bracket width 74 of an acromion process anchoring feature 64 and an acromion arm length 71 of an acromion arm 61 may be configured to match a patient shoulder geometry and effectively locate the acromion process anchoring feature 64 around an acromion base bone 23 with a glenoid cover portion 40 located over a glenoid bone 21. A coracoid bracket width 94 of a coracoid process anchoring feature 84 and a coracoid arm length 91 of a coracoid arm 81 may be configured to match a patient shoulder geometry and effectively locate the coracoid process anchoring feature 84 around the coracoid flange bone 27 with the glenoid cover portion 40 located over the glenoid bone 21.

In an embodiment, a scapular tunnel fastener 32 may extend through the glenoid cover portion 40 and into a scapular tunnel 31 to secure the glenoid cover portion 40 to a scapula 30. The glenoid cover portion 40 may comprise a scapular tunnel anchoring feature 34 to receive the fastener head 33 below or flush with the concave shape 47 of the glenoid cover portion 40. In an embodiment, the scapular tunnel anchoring feature 34 may be aligned with a scapular tunnel 31 of the scapula 30 to facilitate retention of the glenoid implant 14 on the scapula 30 with a scapular tunnel fastener 32 inserted into the scapular tunnel 31. In an embodiment, the scapular tunnel anchoring feature 34 may be configured to prevent friction and wear on a humerus or humerus implant by the fastener head 33 when engaged with the glenoid cover portion 40. In an embodiment, the scapular tunnel fastener 32 may be configured as a screw and the scapular tunnel anchoring feature 34 may be configured as a hole that receives a shank of the screw.

In an embodiment, the glenoid implant 14 and the glenoid cover portion 40 may be further secured and supported by an acromion arch arm 51. The acromion arch arm may be configured to extend from the glenoid cover portion 40 to the acromion arch 222. The extended end of the acromion arch arm 51 may comprise an acromion arch flange 54. In an embodiment, the acromion arch flange 54 may be configured to contact the acromion arch 222. In another embodiment, the acromion arch flange 54 may be configured to be coupled to the acromion arch 222. In an embodiment, a fastener may be inserted through the acromion arch flange 54 to securably connect the acromion arch flange 54 to the acromion arch 222. In an embodiment, a fastener may be inserted through the acromion arch arm 51 to securably connect the acromion arch arm 51 to the acromion arch 222. An acromion arch arm 51 may be configured to constrain the glenoid cover portion 40. In an embodiment, an acromion arch arm 51 may effectively restrain the glenoid cover portion 40 from movement in a superior direction due to forces by the humerus head. The acromion arch arm 51 would be in compression to resist movement of the glenoid cover portion 40 toward the acromion arch 222.

Figure 5:
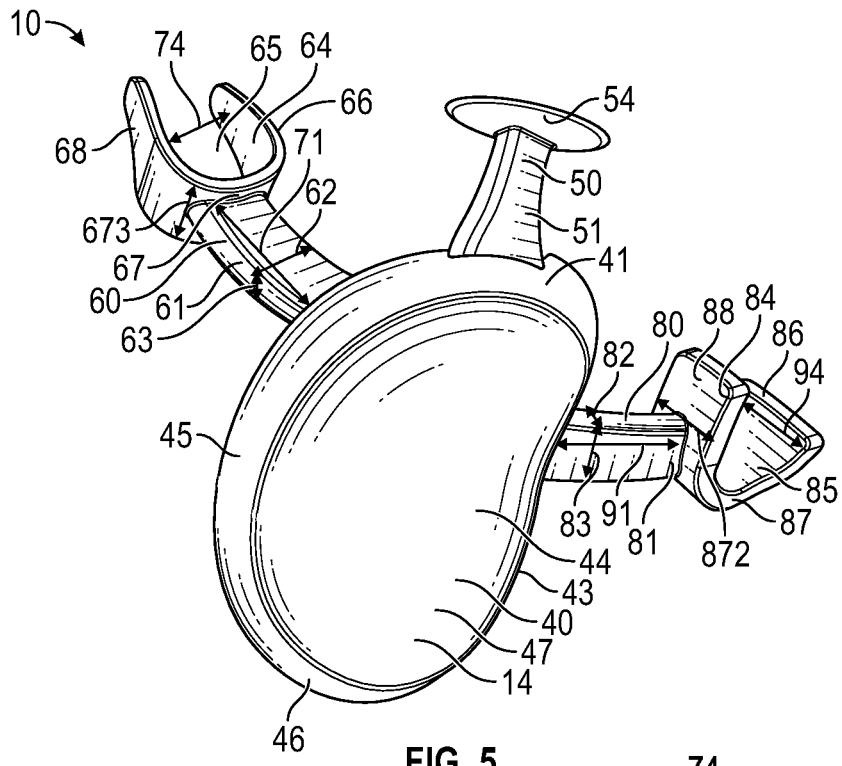
FIG. 5 is a perspective view of a front view of the glenoid replacement system of FIG. 2 comprising a glenoid cover portion that is retained in position by an acromion base retainer and a coracoid flange retainer.
Figure 6:
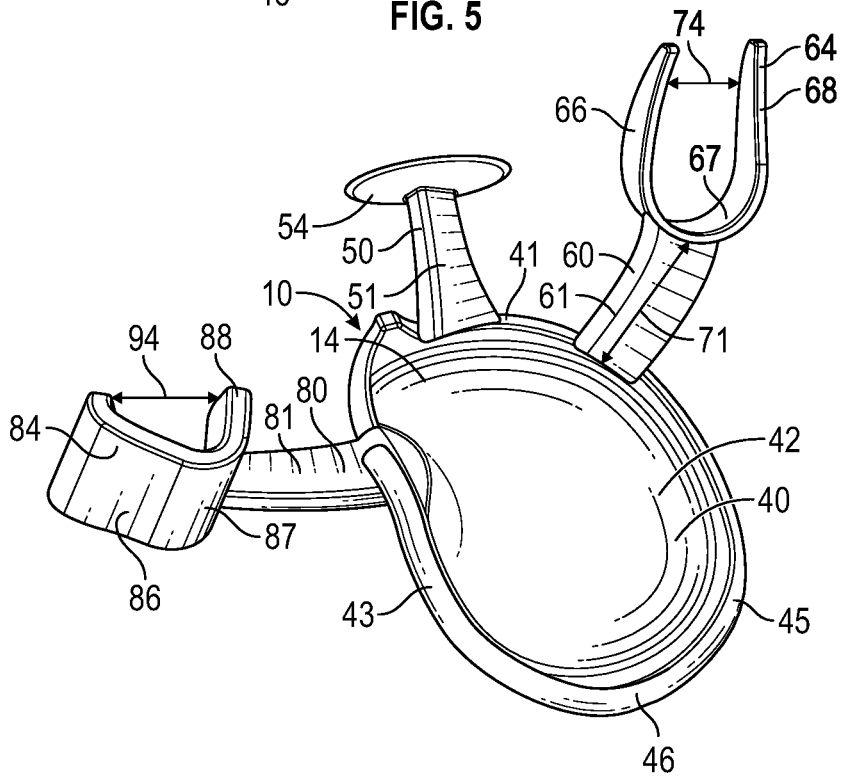
FIG. 6 is a perspective view of a back view of the glenoid replacement system of FIG. 2 comprising a glenoid cover portion that is retained in position by an acromion base retainer and a coracoid flange retainer.
Figure 7:
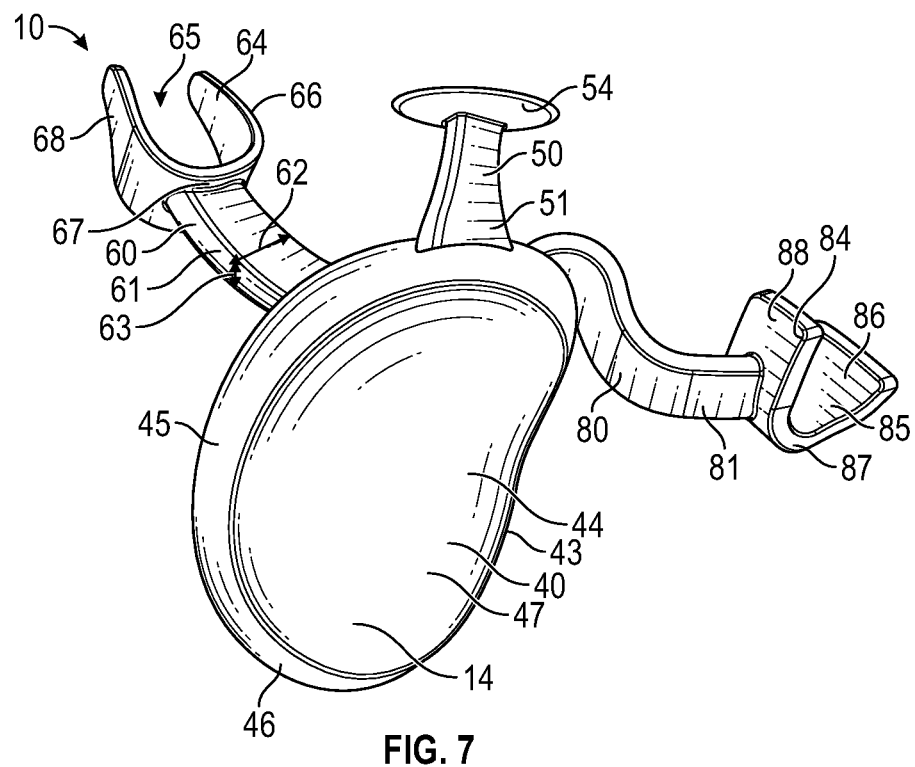
FIG. 7 is a perspective view of a front view of the glenoid replacement system of FIG. 2 comprising a glenoid cover portion that is retained in position by an acromion base retainer and a coracoid flange retainer that extends from a superior portion of the glenoid cover portion.
Figure 8:
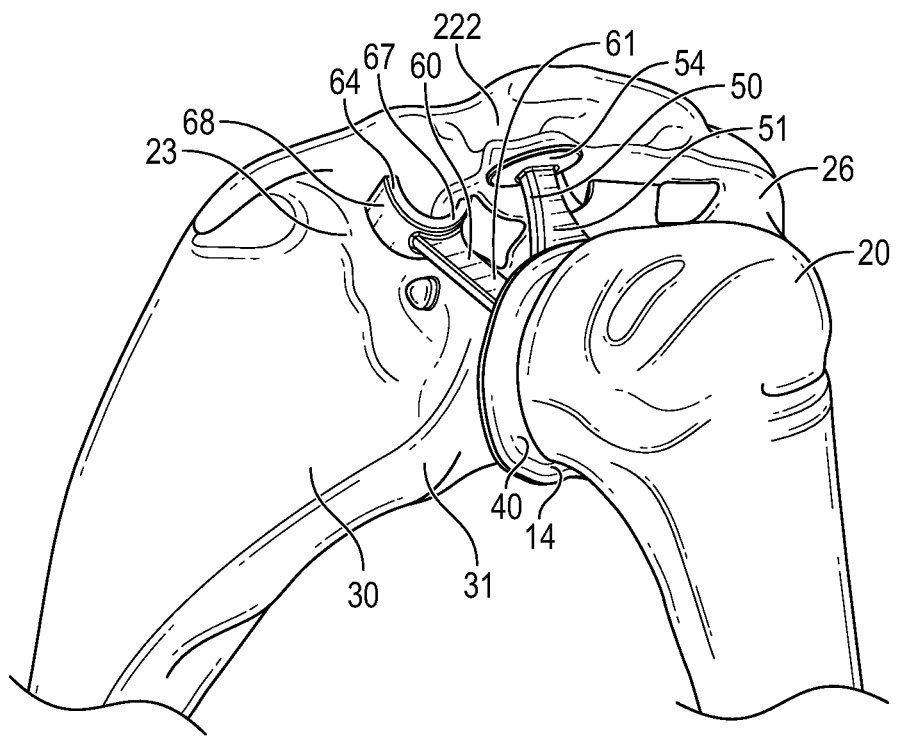
FIG. 8 is a perspective view of a perspective view of the glenoid replacement system of FIG. 2 comprising a glenoid cover portion implanted over the glenoid and retained in position by an acromion base retainer and a coracoid flange retainer (not shown)

In an embodiment, as best shown in FIGS. 5 to 7, an acromion arm 61 may comprise a acromion arm width 62 that may be at least twice the acromion arm height 63 to allow manipulation of an acromion process anchoring feature 64 around the acromion base bone 23 while also providing rigidity. The acromion arm width 62 may be twice or more the acromion arm height 63 which may allow bending in the height direction while reducing bending in the width direction due to the moment of inertia of this geometry. In an embodiment, a coracoid arm 81 may comprise a coracoid arm height 83 that may be at least twice the coracoid arm width 82 to allow manipulation of the coracoid process anchoring feature 84 around the coracoid flange bone 27 while also providing rigidity. The coracoid arm height 83 may be twice or more the coracoid arm width 82 which may allow bending in the width direction while reducing bending in the height direction due to the moment of inertia. Moment of inertia along a rectangular beam in the height (h) direction with respect to a base (b) dimension is $(I=(b \times h^3)/12)$, and therefore a greater height will make a beam much stiffer to flexing along the height direction.

In an embodiment, as best shown in FIGS. 5 to 7, an acromion bracket base 67 may comprise an acromion bracket base height 673 that may be greater by than an acromion arm height 63. In an embodiment, a coracoid bracket base 87 may comprise a coracoid bracket base width 872, that may be greater than the coracoid arm width 82. The acromion bracket base height 673 and the enlarged width along the acromion anterior flange 66 and acromion posterior flange 68 may provide additional surface area to more effectively retain the acromion process anchoring feature 64 to the acromion base bone 23. In an embodiment, a coracoid bracket base width 872 and the enlarged width along the coracoid anterior flange 86 and coracoid posterior flange 88 may provide additional surface area to more effectively retain the coracoid process anchoring feature 84 to the coracoid flange bone 27. In an embodiment, as shown in FIGS. 5 and 6, a coracoid arm 81 may be connected to a glenoid cover portion 40 along a glenoid cover anterior surface 43, opposite the glenoid cover posterior surface 45. FIG. 6 shows the glenoid cover medial surface 42 which may be configured to interface with the glenoid bone 21.

In an embodiment, as shown in FIGS. 4 and 7, a coracoid arm 81 may be connected to a superior portion 41 of the glenoid cover portion 40. Additionally, as shown in FIGS. 5 and 7, the glenoid cover portion 40 may comprise a concave shape 47 along the prosthetic glenoid articular surface 44. The concave shape 47 may be configured to receive a humerus 20 or a prosthetic attached to or over the humerus.

In an embodiment, as shown in FIGS. 2 to 4, a scapular tunnel fastener 32 may extend through a glenoid cover portion 40 and into a scapular tunnel 31 to secure the glenoid cover portion 40 to a scapula 30. The glenoid cover portion 40 may comprise a recessed area to receive a fastener head 33 below or flush with the concave shape 47 of the glenoid cover portion 40.

In an embodiment, as shown in FIGS. 2 to 4, one or more acromion fasteners 69, 69' may be configured to extend through the acromion process anchoring feature 64 and into the acromion base bone 23 to secure the acromion process anchoring feature to the acromion base bone 23. An acromion fastener 69, 69' may be configured to engage any of an acromion anterior flange 66, an acromion posterior flange 68 and/or an acromion bracket base 67. In an embodiment, one or more coracoid fasteners 89, 89' may be configured to extend through the coracoid process anchoring feature 84 and into the coracoid flange bone 27 to secure the coracoid process anchoring feature 84 to the coracoid flange bone 27. A coracoid fastener 89, 89' may be configured to engage any of a coracoid anterior flange 86, a coracoid posterior flange 88 and/or a coracoid bracket base 87.

In an embodiment, the glenoid replacement system 10 may comprise one or more superior anchoring features. The one or more superior anchoring features may be configured to secure a glenoid implant to a scapula. The one or more superior anchoring features may further be configured to limit migration of the glenoid implant on the scapula. The one or more superior anchoring features may be configured to engage parts of the scapula including: a coracoid process, an acromion, an acromion process, a scapular notch, and/or a scapular spine.

Figure 12A:
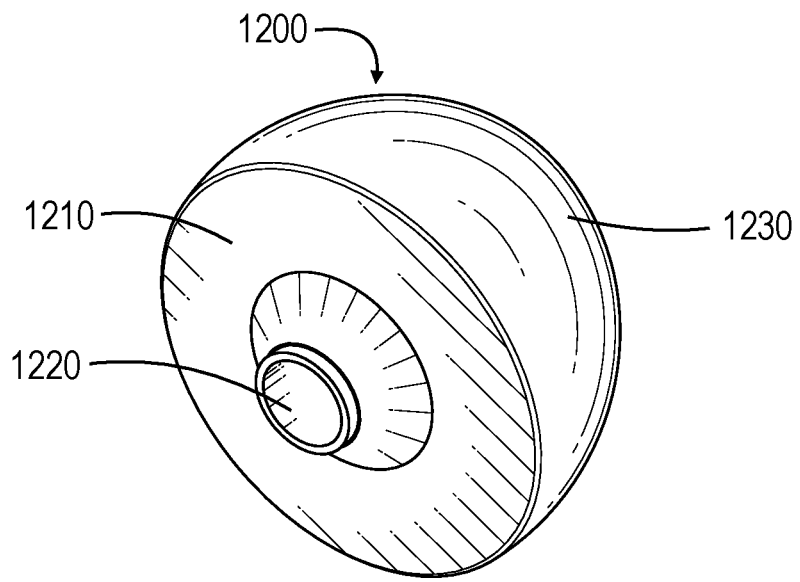
FIG. 12A and FIG. 12B are perspective views of an articulating head component of a glenoid replacement system according to an embodiment.
Figure 12B:
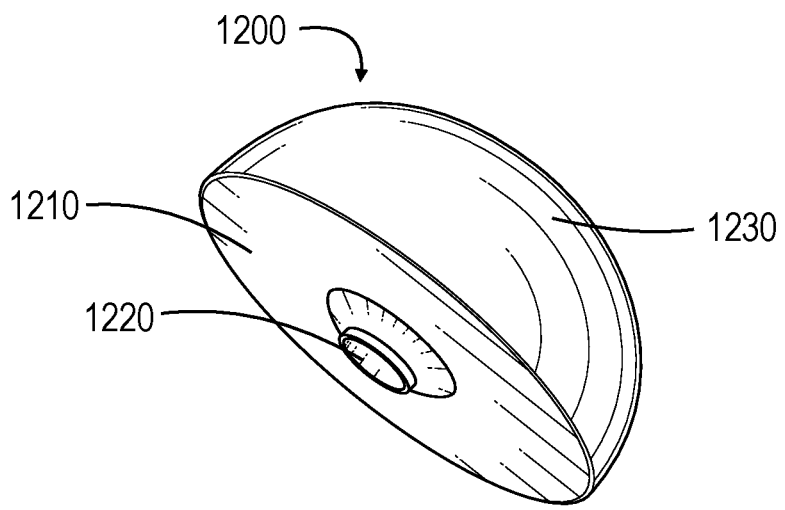

FIG. 12A and FIG. 12B are perspective views of an articulating head component 1200 that may be used in connection with a glenoid replacement system 1400 according to an embodiment. Additionally or alternatively, the articulating head component 1200 may be configured as an anatomic prosthetic humeral articular surface configured to slidably engage a prosthetic glenoid articular surface 44 and to anchor to a humeral metal stem. The articulating head component 1200 may comprise an articulating portion 1210; a trunnion 1220; and an articulating surface 1230. The articulating surface 1230 may be generally convex. In an embodiment, the articulating portion 1210 may be manufactured using a highly crosslinked UHMWPE, a vitamin-E infused highly crosslinked Polyethylene, or other biocompatible polymer. The trunnion 1220 may be manufactured using stainless steel, cobalt chrome, titanium alloy, or other biocompatible material with generally similar mechanical properties. The trunnion 1220 may further be configured with a taper lock surface configured to securably engage a matching tapered recess in the humerus metal stem. The taper lock may be configured with a 12/14 taper, comp ng a proximal diameter of 12 mm, a distal diameter of 14 mm and a length of 20 mm, resulting in a male stem taper angle of 5.725° or 5° 43'30"; a 14/16 taper comprising a truncated cone of 20 mm length with diameters of 14 mm and 16 mm at either end (resulting in a taper angle of 5.725°); or similar taper lock known in the art. In an embodiment, the trunnion 1220 may be configured to be securely bonded to the articulating portion 1210. When used on a humeral implant, the articulating surface 1230 may be configured to articulate with the prosthetic glenoid articular surface 44.

In an embodiment, the articulating head component 1200 may be configured as a glenoid articulating head configured to slidably engage a humeral articular surface and to anchor to a reverse baseplate portion 1420. The articulating head component 1200 may comprise an articulating portion 1210; a trunnion 1220; and an articulating surface 1230. The articulating surface 1230 may be generally convex. In an embodiment, the articulating portion 1210 may be manufactured using a highly crosslinked UHMWPE, a vitamin-E infused highly crosslinked Polyethylene, or other biocompatible polymer. The trunnion 1220 may be manufactured using stainless steel, cobalt chrome, titanium allow, or other biocompatible material with generally similar mechanical properties. The trunnion 1220 may further be configured with a taper lock surface configured to securably engage a matching tapered recess in the reverse baseplate portion 1420. The taper lock may be configured with a 12/14 taper, comprising a proximal diameter of 12 mm, a distal diameter of 14 mm and a length of 20 mm, resulting in a male stem taper angle of 5.725' or 5° 43'30"; a 14/16 taper comprising a truncated cone of 20 mm length with diameters of 14 mm and 16 mm at either end (resulting in a taper angle of 5.725°); or similar taper lock known in the art. In an embodiment, the trunnion 1220 may be configured to be securely bonded to the articulating portion 1210. The articulating surface 1230 may be configured to articulate with a humeral articular surface, which may have a shape similar to that of the prosthetic glenoid articular surface 44.

Figure 13:
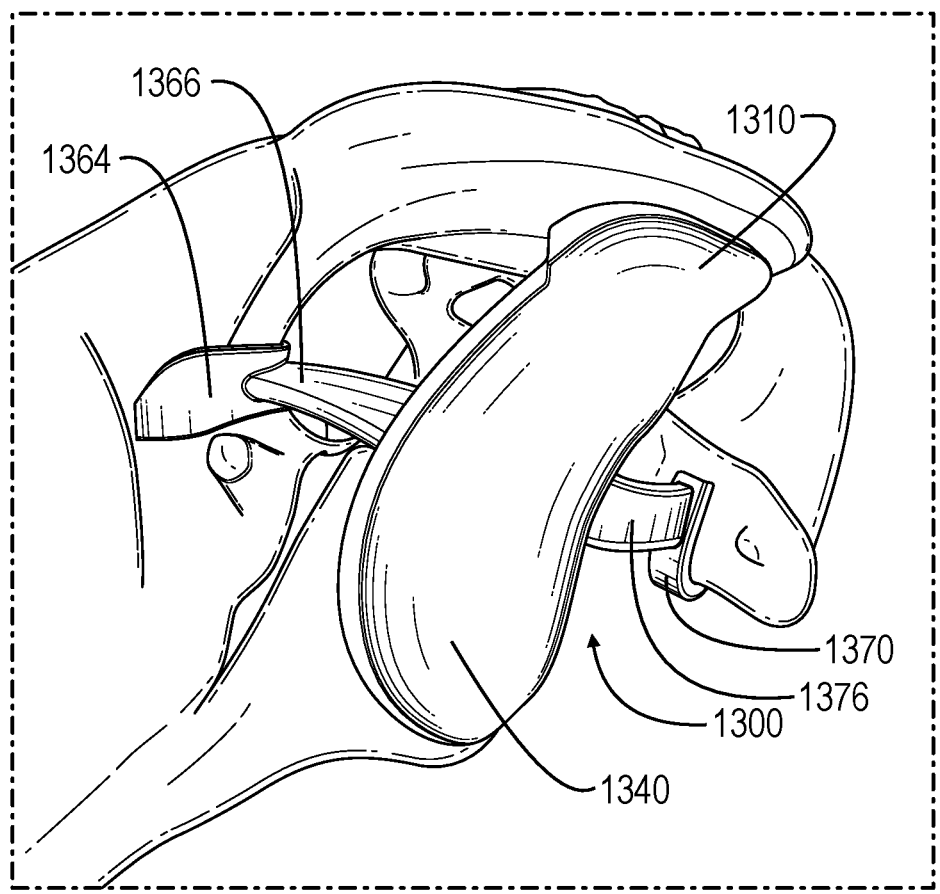
FIG. 13 is a perspective view of a glenoid replacement system implanted over a glenoid bone and coupled with the acromion base bone; the coracoid flange bone; and an acromion arch according to an embodiment.

FIG. 13 is a perspective view of a glenoid replacement system 1300 implanted over a glenoid bone and coupled with the acromion base bone 23, the coracoid flange bone 27, and an acromion arch 222 according to an embodiment. In an embodiment, the glenoid replacement system 1300 may comprise a superior bracing surface 1310 configured such that, with a glenoid implant implanted on a scapula 30, the superior bracing surface 1310 may be oriented superiorly and positioned to abut an acromion arch 222 of the scapula 30 to limit superior migration of the glenoid implant on the scapula 30. The glenoid replacement system 1300 comprising the superior bracing surface 1310 may be configured for cases of complete superior cuff loss (cuff arthropathy). The glenoid replacement system 1300 may comprise a glenoid cover portion 1340 configured to articulate with one of a natural humeral articular surface or an anatomic prosthetic humeral articular surface. The glenoid replacement system 1300 may comprise similar features previously described for glenoid replacement system 10 with the addition of the superior bracing surface 1310. The glenoid replacement system 1300 may further comprise an acromion engaging clamp 1364; an acromion extension arm 1366; a coracoid engaging clamp 1370; and a coracoid extension arm 1376 each comprising similar features previously described.

Figure 14:
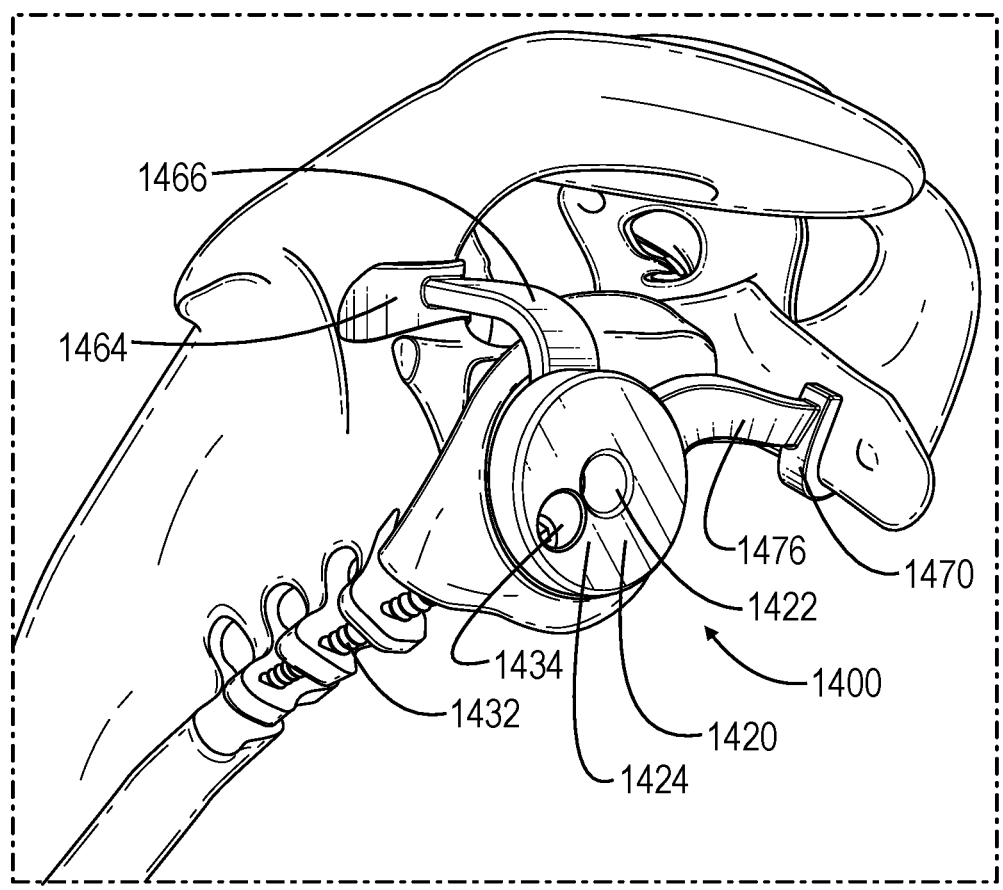
FIG. 14 is a perspective views of a glenoid replacement system implanted over a glenoid bone and coupled with the acromion base bone and the coracoid flange bone according to an embodiment.

FIG. 14 is a perspective view of a glenoid replacement system 1400 implanted over a glenoid bone and coupled with the acromion base bone and the coracoid flange bone according to an embodiment. The glenoid replacement system 1400 may be configured to securably engage an articulating head component 1200 configured as a glenoid articulating head. The glenoid replacement system 1400 securably engaged with the articulating head component 1200 may be configured to articulate with a reverse prosthetic humeral articular surface. The glenoid replacement system 1400 may comprise a reverse baseplate portion 1420 comprising a baseplate aperture 1422; a baseplate face 1424; and a scapular tunnel anchoring feature 1434. The baseplate aperture 1422 may be configured with a taper lock recess configured to securably engage a matching tapered surface of the trunnion 1220. The taper lock may be configured with a 12/14 comprising a proximal diameter of 12 mm, a distal diameter of 14 mm and a length of 20 mm, resulting in a male stem taper angle of 5.725° or 5° 43'30"; a 14/16 taper comprising a truncated cone of 20 mm length with diameters of 14 mm and 16 mm at either end (resulting in a taper angle of 5.725°); or similar taper lock known in the art.

In an embodiment, the reverse baseplate portion 1420 may comprise a scapular tunnel anchoring feature 1434 to receive a scapular tunnel fastener 1432 below or flush with the baseplate face. In an embodiment, the scapular tunnel anchoring feature 1434 may be aligned with a scapular tunnel 31 of the scapula 30 to facilitate retention of the glenoid replacement system 1400 on the scapula 30 with a scapular tunnel fastener 1432 inserted into the scapular tunnel 31. In an embodiment, the scapular tunnel fastener 1432 may be configured as a screw and the scapular tunnel anchoring feature 1434 may be configured as a hole that receives a shank of the screw. The glenoid replacement system 1400 may comprise similar features previously described for glenoid replacement system 10 with the addition of the reverse baseplate portion 1420 in place of the glenoid cover portion 40. The glenoid replacement system 1400 may further comprise an acromion engaging clamp 1464; an acromion extension arm 1466; a coracoid engaging clamp 1470; and a coracoid extension arm 1476 each comprising similar features previously described.

Figure 15:
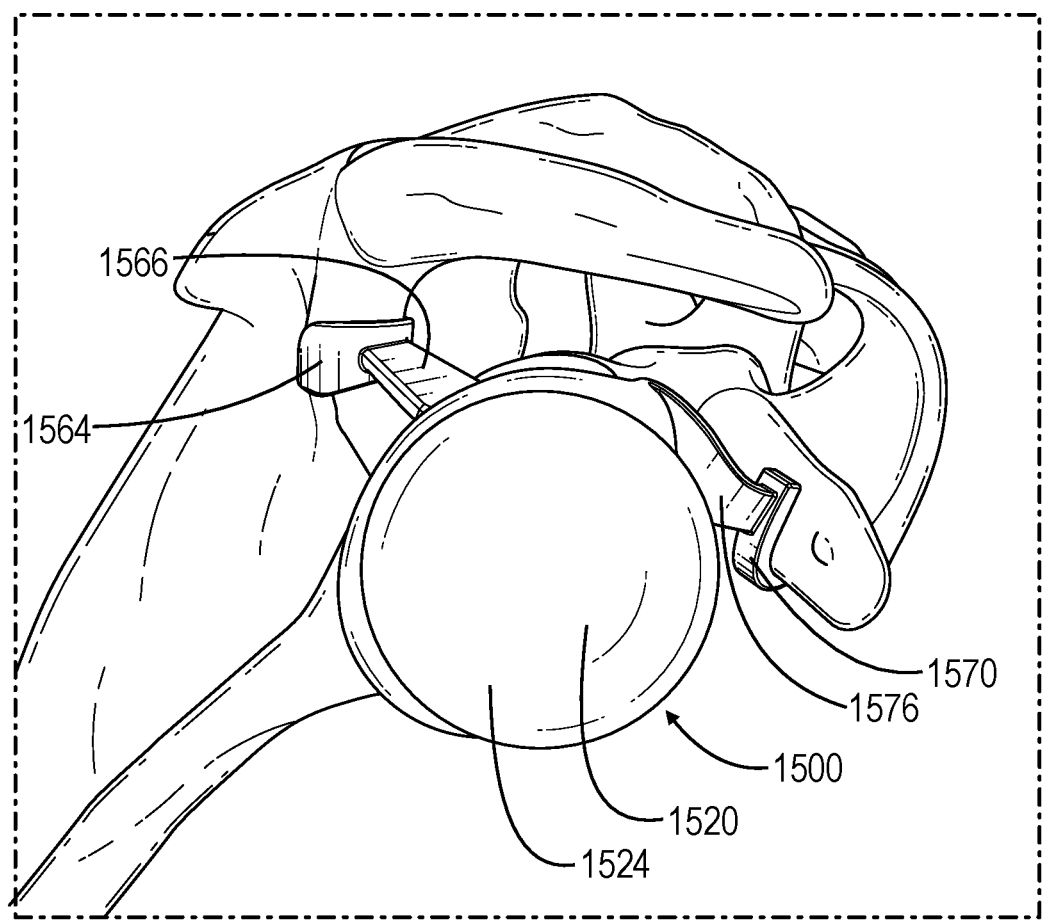
FIG. 15 is a perspective view of a glenoid replacement system implanted over a glenoid bone and coupled with the acromion base bone and the coracoid flange bone according to an embodiment.

FIG. 15 is a perspective view of a glenoid replacement system 1500 implanted over a glenoid bone and coupled with the acromion base bone 23 and the coracoid flange bone 27 according to an embodiment. The glenoid replacement system 1500 may be configured to articulate with a reverse prosthetic humeral articular surface. The glenoid replacement system 1500 may be configured to securably engage an articulating head component 1200 configured as a reverse glenoid portion 1520. Alternatively, the glenoid replacement system 1500 may comprise a reverse glenoid portion 1520 comprising a convex articulating surface 1524 configured to articulate with a reverse prosthetic humeral surface. In an embodiment, the reverse glenoid portion 1520 may be manufactured using a highly crosslinked UHMWPE, a vitamin-E infused highly crosslinked Polyethylene, or other biocompatible polymer. In an embodiment, the reverse glenoid portion 1520 may be configured to be securely bonded to the glenoid replacement system 1500.

The glenoid replacement system 1500 may comprise similar features previously described for glenoid replacement system 10 with the addition of the reverse glenoid portion 1520 in place of the glenoid cover portion 40. The glenoid replacement system 1500 may further comprise an acromion engaging clamp 1564; an acromion extension arm 1566; a coracoid engaging clamp 1570; and a coracoid extension arm 1576 each comprising similar features previously described.

An exemplary method of insertion of a glenoid implant 14 may relate closely to its form and function. The glenoid implant 14, configured to replace the glenoid articular surface of the shoulder's scapula, may comprise arms extending to adjacent bony protuberances for better fixation. These arms may expand the horizontal dimension of the glenoid implant 14 over conventional glenoid replacements. Installation of the new glenoid implant 14 through the preferred surgical approach may require special steps and implant design.

The steps of implantation may protect the soft tissues from additional trauma from the extended arms of the device while accomplishing the press-in interference fit of the acromion process anchoring feature 64 and the coracoid process anchoring feature 84 to the bony protuberances. Fixation by interference fit may reduce or avoid the need for holes being formed through the bone for primary fixation with screws, which may weaken the narrow bony protuberances that support muscles and the joint surface of the shoulder.

An exemplary method steps of inserting the glenoid implant 14 may be as follows. A standard surgical incision may be made at the anterolateral shoulder extending into the shoulder joint space and the articular portion of the humeral head may be removed as may be done for all shoulder replacements in common use. Next, with space available to access the glenoid articular surface, the glenoid articular cartilage may be removed by milling and the underlying bone may be reshaped as needed. The glenoid implant 14 may be implanted next, with the help of a holding device. An exemplary holding device may bend and compress the glenoid implant 14 and/or the acromion arm 61 and coracoid arm 81 to enable insertion through a smaller incision.

In an embodiment, a glenoid implant 14 may be inserted into an incision whereby an acromion process anchoring feature 64 and acromion arm 61 may be inserted first. A tip of the acromion process anchoring feature 64 may comprise an acromion anterior flange 66 and an acromion posterior flange 68 configured to slide over a vertical column of bone of the acromion base bone 23. The acromion process anchoring feature 64 may be sized to fit loosely and to slide in and out on the bone column. The acromion process anchoring feature 64 may be configured to engage the acromion base bone 23 while the glenoid cover portion 40; the coracoid arm 81 and coracoid process anchoring feature 84 remain outside of the incision. In an embodiment, the acromion process anchoring feature 64 may be configured to engage the acromion base bone 23 to guide the glenoid cover portion 40; the coracoid arm 81; and coracoid process anchoring feature 84 into the incision. The acromion process anchoring feature 64 may be configured for an interference fit as it is slid up and into position on the acromion base bone 23.

In an embodiment, a glenoid cover portion 40 may be inserted through a longitudinal incision into the shoulder joint space with the coracoid arm 81 and coracoid process anchoring feature 84 following in alignment with the longitudinal incision. As the coracoid process anchoring feature 84 is advanced into the shoulder space, the glenoid cover portion 40 of the glenoid implant 14 may translate posteriorly into the joint space, allowing the coracoid arm 81 to move into the joint space. In an embodiment, delivery of the coracoid arm 81 may be aided by tissue retraction and the back and forth sliding action of the glenoid implant 14 along the acromion base bone 23. In some embodiment, a glenoid implant 14 may comprise a telescoping mechanism configured to provide additional play for ease of insertion or in cases of special clinical need. In an embodiment, the acromion arm 61 may comprise one or more nesting tubular sections or another design of telescoping structure.

In an embodiment, a next step in a method of implanting a glenoid implant 14 may be to attach a coracoid process anchoring feature 84 to a coracoid process 26. Movement of the coracoid process anchoring feature 84 along the coracoid process 26 during the attachment maneuver may be permitted because of sliding action of the acromion process anchoring feature 64 on the acromion base bone 23 and the free travel of the prosthetic glenoid articular surface 44 across the glenoid bone 21. In an embodiment, the coracoid arm 81 may be delivered deep into the subscapularis tendon in the anterior shoulder joint cavity and then may be directed anteriorly towards the coracoid process 26. In an embodiment, the coracoid arm may be expanded to the full extent of its travel and may be delivered deep into the subscapularis tendon in the anterior shoulder joint cavity and then may be directed anteriorly towards the coracoid process 26. The coracoid process anchoring feature 84 may be slid beneath the coracoid process 26 to hook around the circular-shaped hard boney stalk of the coracoid process.

In an embodiment, the coracoid arm 81 may comprise an effective amount of mechanical flex to provide the necessary deflection for positioning a coracoid process anchoring feature 84 over a coracoid process 26. The coracoid arm width 82 and coracoid arm height 83 may have a ratio to enable this flexure or deflection while providing effective support of the glenoid cover portion 40, as described herein. The coracoid arm width 82 may be some fraction of the coracoid arm height 83, such as about 0.75 or less, about 0.5 or less, or even 0.33 or less, for example. The coracoid arm 81 geometry may be configured to support the downward bending or deflection upon insertion and elastic return under pressure. The coracoid arm 81 geometry, while allowing for insertion by press fit, does not detract from the purpose of resisting the entire glenoid implant 14 anteroposterior and torsional motion in a manner far superior to existing implants.

In an embodiment, the fit of acromion process anchoring feature 64 to the native acromion base bone 23 may be modified by the size, shape, and separation of the acromion anterior flange 66 and acromion posterior flange 68. Further, the fit of acromion process anchoring feature 64 to the native acromion base bone 23 may be modified by the change in approach angle of the acromion process anchoring feature 64 as the coracoid process anchoring feature 84 may be redirected towards the coracoid anteriorly as the coracoid process anchoring feature 84 is coupled to the coracoid process 26. In an embodiment, the glenoid implant 14 may be moved anteriorly to secure the coracoid process anchoring feature to the coracoid bone. As the glenoid implant 14 is moved anteriorly, the acromion process anchoring feature 64 may slide on the acromion base bone 23 as necessary. The translation of the acromion process anchoring feature 64 may be in a direction opposite to the initial direction along the acromion base bone 23. Because the acromion base bone 23 in most patients may not be truly round, the change in the acromion process anchoring feature approach may create a cinching of the interface between the acromion process anchoring feature 64 and the acromion base bone 23. In an embodiment, if a glenoid cover portion 40 is tilted into its final position over a glenoid bone 21, additional cinching of the interference fit by the acromion process anchoring feature 64 on the acromion base bone 23 may occur. A final step of seating of a glenoid implant 14 may comprise placement of one or more fixation fasteners through the glenoid implant 14 and into the subchondral bone. The degree of cinching interference fit created at the acromion process anchoring feature shaped clamp may be mapped predictably by combining test data with engineering principles of fit according to patient contours.

An exemplary method of implanting a glenoid implant 14 through a conventional incision may employ specific geometries as described hereafter. As the glenoid implant 14 is advanced into the shoulder joint it may be kept in alignment with the incision to take advantage of the length of the incision which exceeds the width of the incision and may allow the glenoid cover portion 40 of the glenoid implant 14 to be aligned with a patient's anatomy to facilitate positioning in the joint space. In an embodiment, alignment of the glenoid cover portion 40 over the joint cavity may be facilitated by rotation of the acromion process anchoring feature 64 on the acromion base bone 23 within the constraints created by engagement of the acromion anterior flange 66 and the acromion posterior flange 68 with the acromion base bone 23. As the acromion process anchoring feature 64 is advanced, it may have a rotational position that is altered from an ideal for glenoid cover portion 40 insertion. For this reason, the acromion process anchoring feature 64 may comprise a spiral shape. The spiral shape and the distance between the acromion anterior flange 66 and the acromion posterior flange 68 may both be variable that may be related to the specific anatomy of a patient under treatment for ideal fitment. Additionally, the geometry of the glenoid implant 14 may be related to the specific anatomy of a patient under treatment for ideal fitment. In an embodiment, a glenoid replacement system 10 may be altered according to patient-specific data which may be acquired using anatomical data acquisition in 3D from each patient. This data may be interpreted by comparison to that obtained during implant testing, with potential revision according to surgeon experience and may include surgeon experience with a range of patient sizes.

In an embodiment, geometry of a glenoid replacement system 10 and method of insertion of a glenoid replacement system 10 may comprise logarithmic machine-assisted patient-specific implant design methodology which may provide additional benefits. Fixation of the glenoid replacement system 10 to adjacent bones via extension arms (including an acromion arm 61; a coracoid arm 81; and/or an acromion arch arm 51) may provide improved fixation to support reliable bone ingrowth for permanent biological fixation of the glenoid implant 14. An exemplary glenoid implant 14 as described herein may be implanted without creating additional trauma during insertion. The exemplary glenoid replacement system 10 and method of insertion of a glenoid replacement system 10 may offer a solution to patients with failed prior implants or other sources of glenoid bone loss, for whom the auxiliary fixation of the articular surface by a guided screw into the scapular tunnel may be a key component. For patients lacking a functional rotator cuff, the superior extension of the glenoid replacement system 10 may include an auxiliary extension configured to provide acromion arch contact support and may provide longer-term durability while enabling the use of glenoid designs having built-in mechanical constraints against superior head migration. The glenoid replacement system 10 may be configured to provide normal joint biomechanics. In an embodiment, the glenoid replacement system 10 may be configured such that the interference fit of the acromion process anchoring feature 64 and the coracoid process anchoring feature 84 may enable the use of no more than relatively small locking screws as safety locks against clamp disconnection from bone.

Figure 9A:
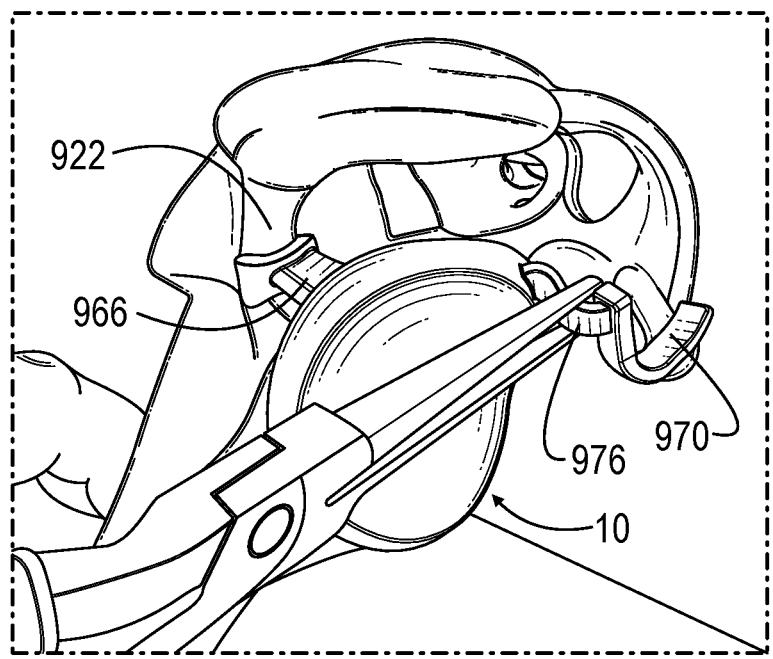
FIG. 9A through FIG. 9D are perspective views of steps for implantation of a glenoid replacement system according to an embodiment, showing a straight-in view at the anterolateral shoulder, which resembles the view seen by surgeons during insertion.
Figure 9B:
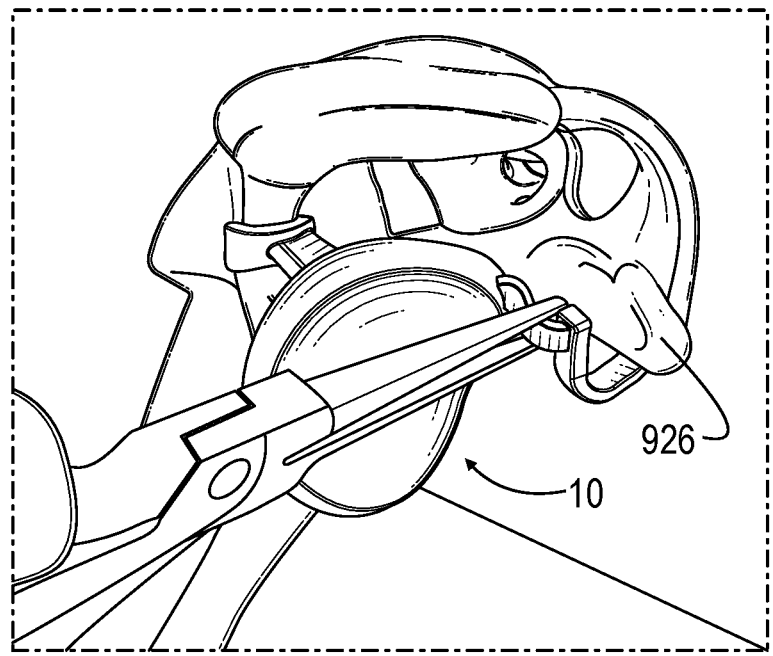
Figure 9C:
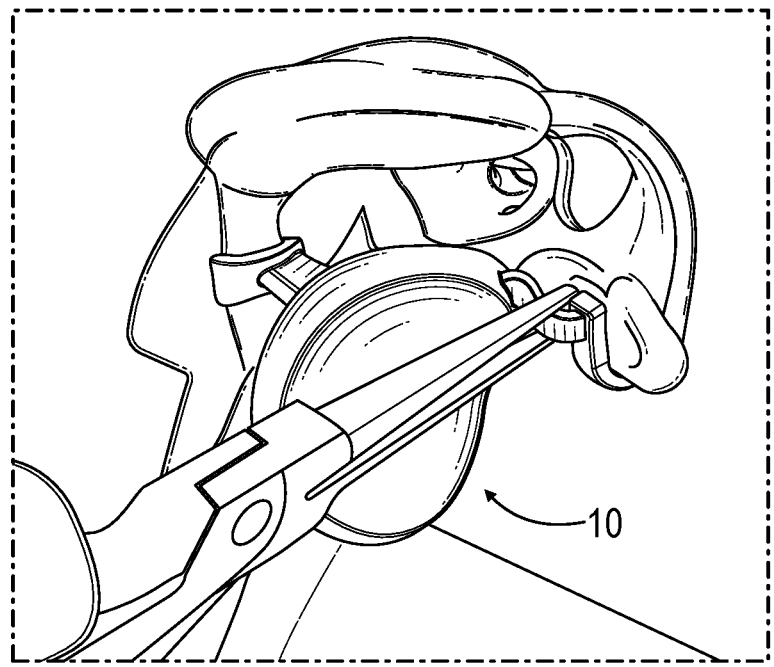
Figure 9D:
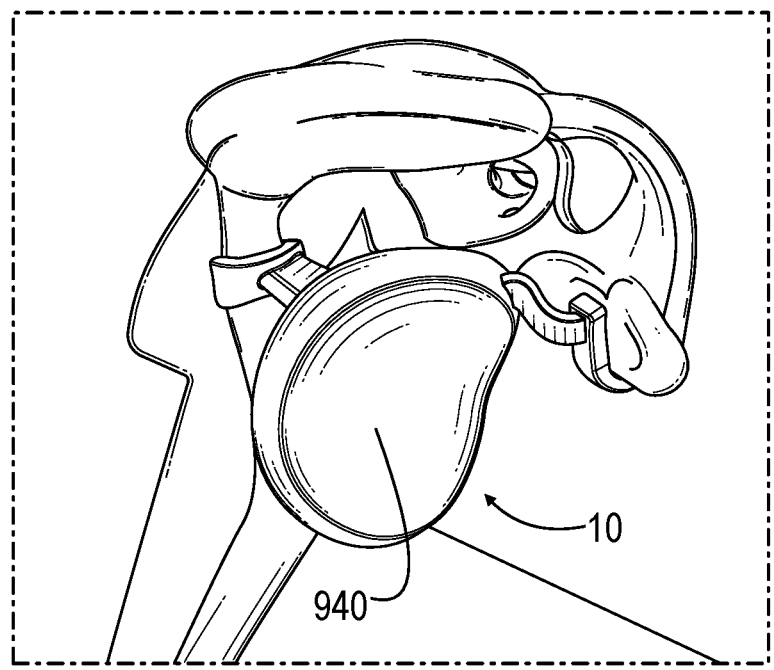
Figure 10A:
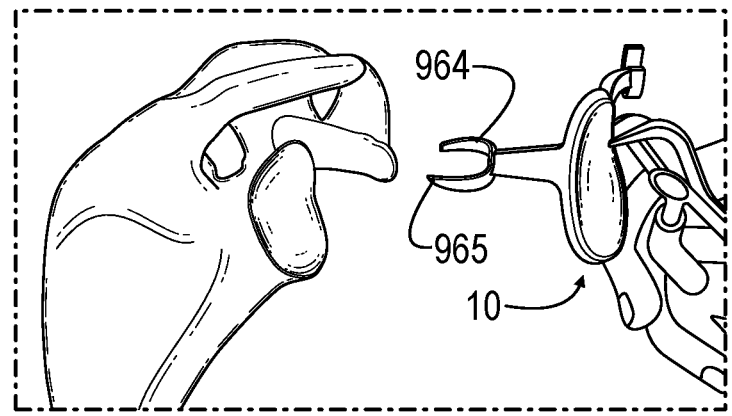
FIG. 10A through FIG. 10G are perspective views of steps for implantation of a glenoid replacement system according to an embodiment, showing a posteriolateral view of a shoulder.
Figure 10B:
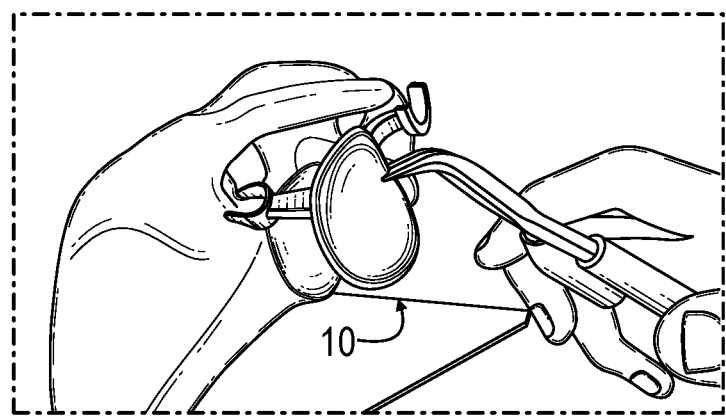
Figure 10C:
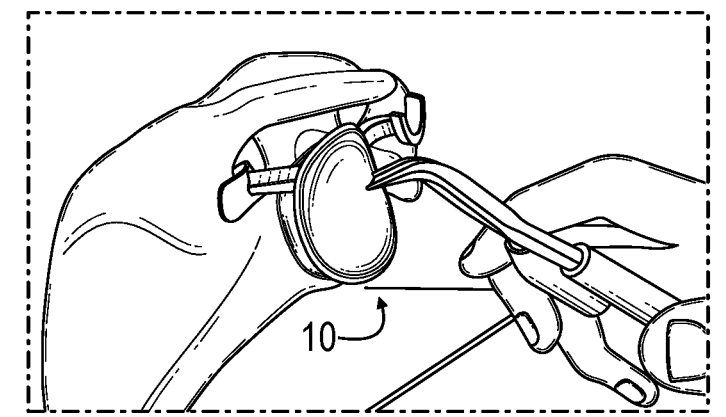
Figure 10D:
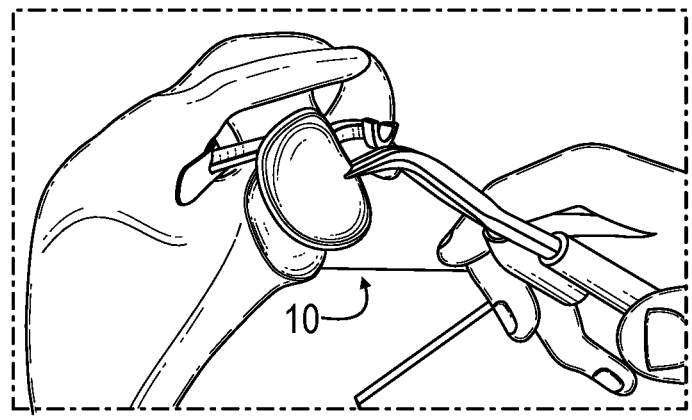
Figure 10E:
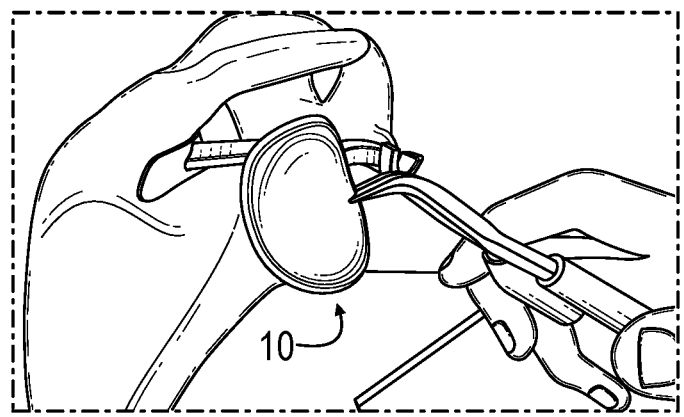
Figure 10F:
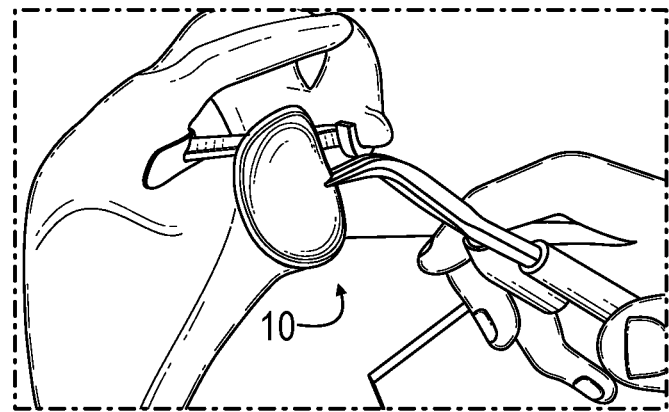
Figure 10G:
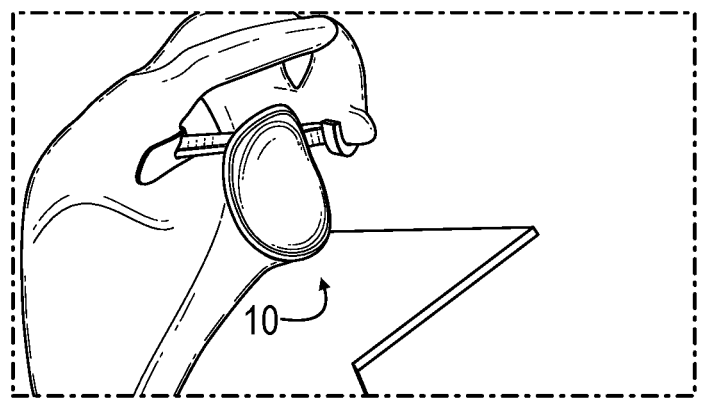
Figure 11A:
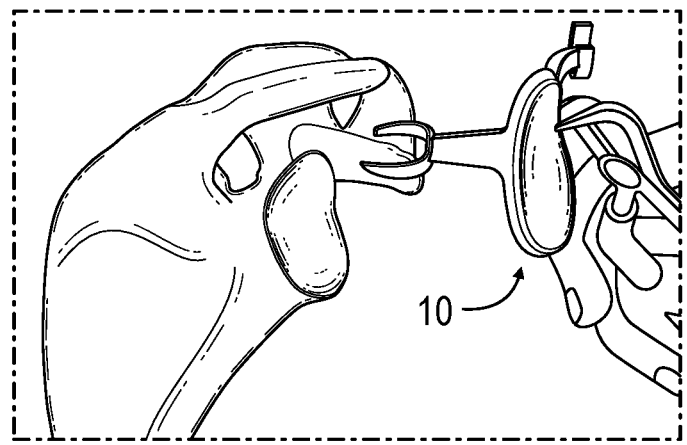
FIG. 11A through FIG. 11E are perspective views of steps for implantation of a glenoid replacement system according to an embodiment, showing a posteriolateral view of a shoulder.
Figure 11B:
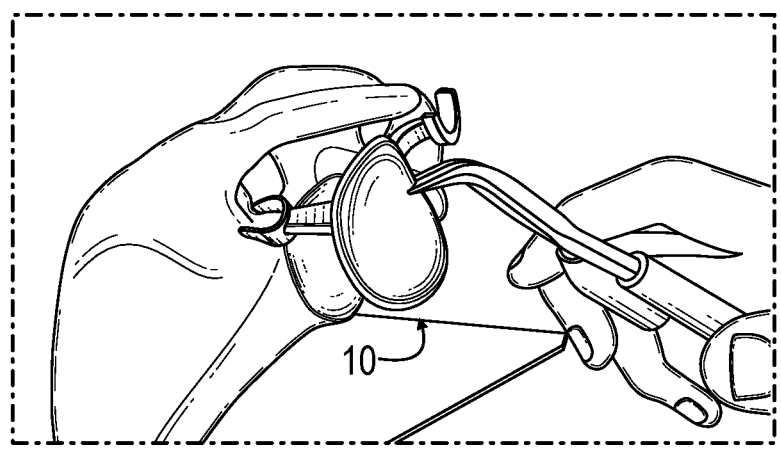
Figure 11C:
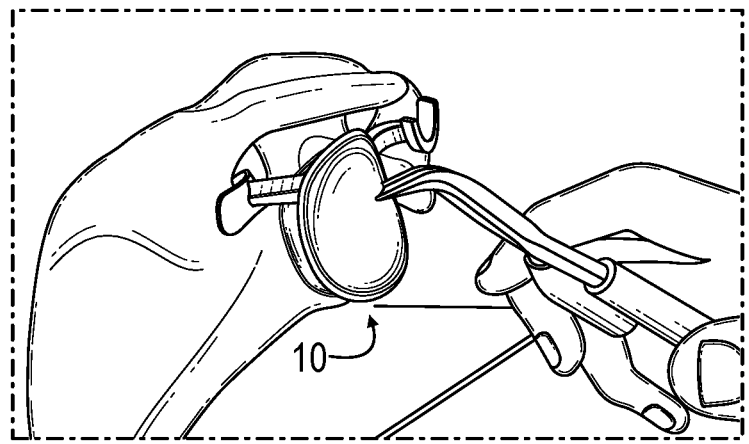
Figure 11D:
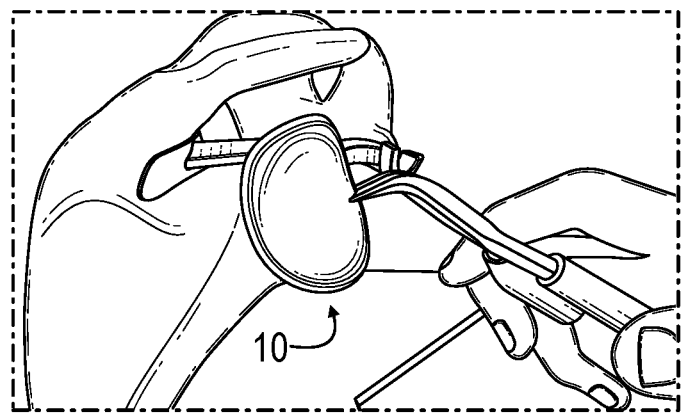
Figure 11E:
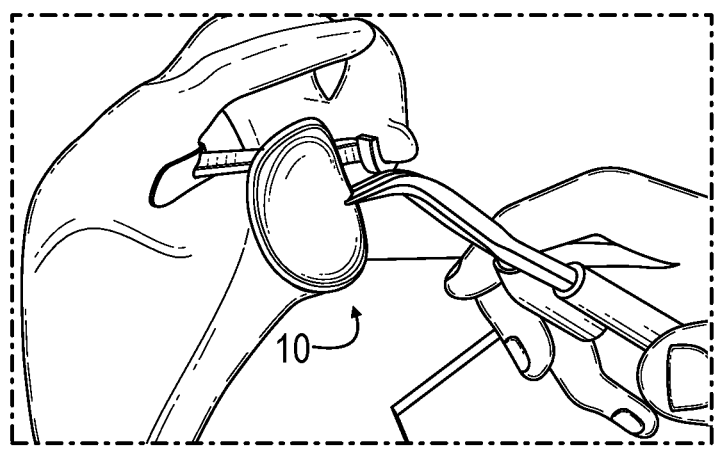

FIG. 9A though FIG. 9D, FIG. 10A through FIG. 10G, and FIG. 11A through FIG. 11E illustrate one exemplary method for implantation of a glenoid replacement system 10 according to an embodiment. The method for implanting the glenoid replacement system 10 may include the following steps:

1. An acromion engaging clamp 964 may be advanced first, and may engage a hard rounded edge of an acromion process 922 approximately half way up the base of the acromion process 922. An acromion engaging clamp tip 965 may comprise widened blunt tips to enable tactile guidance for acromion engagement. The acromion engaging clamp 964 may be configured as a clothes pin-shaped clamp and may be intentionally wider than the acromion base to allow sliding of the acromion engaging clamp 964 on the acromion process 922.

2. As the acromion engaging clamp 964 slides in over the acromion process 922, a glenoid cover portion 940 may advance deeper into the wound as well. A torsional shape designed into an acromion extension arm 966 may guide the glenoid cover portion 940 inferiorly with advancement until the glenoid cover portion 940 comes to rest on the central and posterior portion of the glenoid articular surface.

3. The acromion engaging clamp 964 may be configured to permit movement of the acromion engaging clamp 964 on the acromion process 922 as the advancement of the device may next be directed towards the coracoid process 926 to engage the tip of a coracoid engaging clamp 970 and the posterior cortical surface of the coracoid process 926.

4. Coracoid engagement is next, as the glenoid replacement system 10 may then be advanced anteriorly to engage the coracoid process 926, while a coracoid engaging clamp 970 may be directed beneath the coracoid process 926. As the glenoid replacement system 10 advances, the glenoid replacement system 10 may lock into position around the coracoid process 926. In this position, flex in the acromion extension arm 966 and the coracoid extension arm 976 may generate a compression force applied to the cover plate against the upper glenoid articular surface.

5. The final step may be optional fastener fixation of a glenoid cover portion 940, using guided fastener placement into the scapular tunnel.

Those of skill in the art will recognize that this is only one of many potential methods that may be used to implant a glenoid replacement system, such as the glenoid replacement system 10. In alternative embodiments, different methods may be used to implant the glenoid replacement system 10 or other systems described above. Further, the method set forth in FIG. 9A though FIG. 9D, FIG. 10A through FIG. 10G, and FIG. 11A through FIG. 11E may be used to implant other glenoid replacement systems besides those specifically disclosed herein.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. Moreover, as defined herein the term "substantially" means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, instruments, and methods disclosed herein.

What is claimed is:

1. A method for securing a glenoid implant to a scapula of a patient, the method comprising:
    positioning a glenoid implant proximate the scapula, the glenoid implant comprising a prosthetic glenoid articular surface and a scapular tunnel anchoring feature;
    positioning the glenoid implant on the scapula such that the prosthetic glenoid articular surface is positioned to articulate with one of:
        a natural humeral articular surface;
        an anatomic prosthetic humeral articular surface; and
        a reverse prosthetic humeral articular surface; and
    anchoring the glenoid implant to the scapula by inserting a scapular tunnel fastener into a scapular tunnel of the scapula to secure the scapular tunnel anchoring feature relative to the scapular tunnel.

2. The method of claim 1, wherein the scapular tunnel fastener comprises a screw and the scapular tunnel anchoring feature comprises a hole that receives a shank of the screw.

3. The method of claim 1, further comprising: securing a first superior anchoring feature comprising one of a coracoid process anchoring feature and an acromion process anchoring feature.

4. The method of claim 3, wherein the first superior anchoring feature comprises a clamp, the method further comprising: engaging the scapula with the clamp prior to positioning the glenoid implant on the scapula.

5. The method of claim 3, further comprising: securing a second superior anchoring feature comprising the other of the coracoid process anchoring feature and the acromion process anchoring feature.

6. A method for securing a glenoid implant to a scapula of a patient, the method comprising:
    positioning a glenoid implant proximate the scapula, the glenoid implant comprising a prosthetic glenoid articular surface and a scapular tunnel anchoring feature;
    positioning the glenoid implant on the scapula such that the prosthetic glenoid articular surface is positioned to articulate with one of:
        a natural humeral articular surface;
        an anatomic prosthetic humeral articular surface; and
        a reverse prosthetic humeral articular surface; and
    anchoring the glenoid implant by engaging a first superior anchoring feature selected from a group consisting of:
        a coracoid process anchoring feature configured to secure the glenoid implant to a coracoid process of the scapula; and
        an acromion process anchoring feature configured to secure the glenoid implant to an acromion process of an acromion of the scapula.

7. The method of claim 6, wherein the first superior anchoring feature comprises the coracoid process anchoring feature comprising a coracoid clamp configured to grip the coracoid process.

8. The method of claim 7, wherein the coracoid process anchoring feature further comprises one or more apertures configured to receive one or more fasteners configured to secure the coracoid process anchoring feature to the coracoid process, the method further comprising: anchoring the glenoid implant to the scapula by inserting the one or more fasteners into the coracoid process of the scapula to secure the coracoid process anchoring feature relative to the coracoid process.

9. The method of claim 6, wherein the first superior anchoring feature comprises the acromion process anchoring feature comprising an acromion clamp configured to grip the acromion process.

10. The method of claim 9, wherein the acromion process anchoring feature further comprises one or more apertures configured to receive one or more fasteners configured to secure the acromion process anchoring feature to the acromion process, the method further comprising: anchoring the glenoid implant to the scapula by inserting the one or more fasteners into the acromion process of the scapula to secure the acromion process anchoring feature relative to the acromion process.

11. The method of claim 10, further comprising: securing a second superior anchoring feature comprising a coracoid clamp configured to grip the coracoid process.

12. The method of claim 9, wherein engagement of the acromion clamp permits movement of the acromion process anchoring feature relative to the acromion process and allows the glenoid implant to be rotated into position proximate the scapula.

13. A method for securing a glenoid implant to a scapula of a patient, the method comprising:
   positioning a glenoid implant proximate the scapula, the glenoid implant comprising a prosthetic glenoid articular surface and a scapular tunnel anchoring feature;
   positioning the glenoid implant on the scapula such that the prosthetic glenoid articular surface is positioned to articulate with one of:
      a natural humeral articular surface;
      an anatomic prosthetic humeral articular surface; and
      a reverse prosthetic humeral articular surface; and
   anchoring the glenoid implant by engaging a superior bracing surface configured such that, with the glenoid implant implanted on the scapula, the superior bracing surface is oriented superiorly and positioned to abut an acromion of the scapula to limit superior migration of the glenoid implant on the scapula.

14. The method of claim 13, wherein the superior bracing surface is part of an acromion process anchoring feature configured to anchor the glenoid implant to the acromion.

15. The method of claim 14, wherein the acromion process anchoring feature comprises a clamp configured to grip an acromion process of the acromion.

16. A method for securing a glenoid implant to a scapula of a patient, the method comprising:
   positioning a glenoid implant proximate the scapula, the glenoid implant comprising a prosthetic glenoid articular surface and a scapular tunnel anchoring feature;
   positioning the glenoid implant on the scapula such that the prosthetic glenoid articular surface is positioned to articulate with one of:
      a natural humeral articular surface;
      an anatomic prosthetic humeral articular surface; and
      a reverse prosthetic humeral articular surface; and
   anchoring a first clamp configured to grip a bony protuberance of the scapula to secure the glenoid implant relative to the bony protuberance.

17. The method of claim 16, wherein the first clamp is positioned to grip an acromion process of an acromion of the scapula.

18. The method of claim 16, wherein the first clamp is positioned to grip a coracoid process of the scapula.

19. The method of claim 18, further comprising: engaging a second clamp configured to grip an acromion process of an acromion of the scapula.

* * * * *